United States Patent
Thomas et al.

(10) Patent No.: US 6,908,920 B2
(45) Date of Patent: Jun. 21, 2005

(54) PYRIMIDINE DERIVATIVES

(75) Inventors: Andrew Peter Thomas, Macclesfield (GB); Nicholas John Newcombe, Macclesfield (GB); David William Heaton, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/332,275

(22) PCT Filed: Jul. 6, 2001

(86) PCT No.: PCT/GB01/03084

§ 371 (c)(1), (2), (4) Date: Jan. 7, 2003

(87) PCT Pub. No.: WO02/04429

PCT Pub. Date: Jan. 17, 2002

(65) Prior Publication Data

US 2003/0216406 A1 Nov. 20, 2003

(30) Foreign Application Priority Data

Jul. 11, 2000 (GB) .............................................. 0016877

(51) Int. Cl.$^7$ .................... C07D 413/12; C07D 403/12; C07D 239/48; A61K 31/505; A61K 31/506

(52) U.S. Cl. .............................. 514/235.8; 514/252.14; 514/252.18; 514/252.19; 514/252.2; 514/275; 544/122; 544/295; 544/323; 544/324

(58) Field of Search .................... 514/235.8, 252.14, 514/275, 252.18, 252.19, 252.2; 544/123, 295, 323, 122, 324

(56) References Cited

U.S. PATENT DOCUMENTS

| | | | |
|---|---|---|---|
| 4,983,608 A | 1/1991 | Effland et al. | 514/216 |
| 5,516,775 A | 5/1996 | Zimmermann et al. | 514/224.2 |
| 5,521,184 A | 5/1996 | Zimmermann | 514/252 |
| 5,610,303 A | 3/1997 | Kimura et al. | 544/326 |
| 5,739,143 A | 4/1998 | Adams et al. | 514/275 |
| 5,859,041 A | 1/1999 | Liverton et al. | 514/396 |
| 6,593,326 B1 * | 7/2003 | Bradbury et al. | 514/235.8 |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 B1 | 8/1990 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |

(Continued)

OTHER PUBLICATIONS

Draetta, G. and Pagano, M. in "Annual Reports in Medicinal Chemistry, vol. 31", 1996, Academic Press, San Diego, p 241–246.*

S. Mani; C. Wang; K. Wu; R. Francis; R. Pestell Expert Opinion on Investigational Drugs 2000, vol. 9, No. 8, pp. 1849–1870, abstract only.*

Kimball, D.S. et al, Ann. Reports Med. Chem., vol. 36, 2001, pp. 139–148.*

J. Dumas, Expert Opinion on Therapeutic Patents, 2001, vol. 11, No. 3, pp. 405–429, abstract only.*

Boschelli et al., "Synthesis A. Tyrosine Kinase Inhibitory Activity of A Serie of 2–Amino–8H–Pyrido'2,3–Dipyrimidines:", Journal of Medicinal Chemistry, vol. 41, No. 22, 1998, pp. 4365–4377.

(Continued)

*Primary Examiner*—Thomas C. McKenzie
(74) *Attorney, Agent, or Firm*—Morgan, Lewis & Bockius LLP

(57) ABSTRACT

Compounds of formula (I), wherein $R^1$, p, $R^2$, q, $R^3$ and $R^4$ are defined within, and a pharmaceutically acceptable salts and in vivo hydrolysable esters are described. Also described are processes for their preparation and their use as medicaments, particularly medicaments for producing a cell cycle inhibitory (anti-cell-proliferation) effect in a warm-blooded animal, such as man (I)

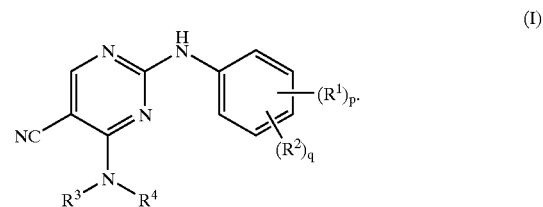

10 Claims, No Drawings

U.S. PATENT DOCUMENTS

| WO | 99/41253 | 8/1999 |
|---|---|---|
| WO | 99/50250 | 10/1999 |
| WO | 99/50251 | 10/1999 |
| WO | 00/12485 | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 | 7/2000 |
| WO | 00/44750 | 8/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/14375 A1 | 3/2001 |
| WO | 01/29009 A1 | 4/2001 |
| WO | 01/30778 A1 | 5/2001 |
| WO | 01/37835 A1 | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 01/72717 A1 | 10/2001 |
| WO | 02/20512 A1 | 3/2002 |
| WO | 02/066481 A1 | 8/2002 |
| WO | 02/096887 A1 | 12/2002 |

OTHER PUBLICATIONS

U.S. Appl. No. 09/763,705, filed Feb. 26, 2001, Breault et al., PCT Publication No. WO 00/12485, PCT Publication Date Mar. 9, 2000.

U.S. Appl. No. 09/763,681, filed Feb. 26, 2001, Breault et al., PCT Publication No. WO 00/12486, PCT Publication Date Mar. 9, 2000.

U.S. Appl. No. 09/868,602, filed Jun. 20, 2001, PCT Publication No. WO 00/39101, PCT Publication Date Jul. 6, 2000.

U.S. Appl. No. 09/914,788, filed Sep. 5, 2001, Breault et al., PCT Publication No. WO 00/53595, PCT Publication Date Sep. 14, 2000.

U.S. Appl. No. 09/958,077, filed Oct. 4, 2001, Breault, PCT Publication No. WO 00/59892, PCT Publication Date Oct. 12, 2000.

U.S. Appl. No. 10/203,154 (allowed Jun. 27, 2003), filed Aug. 6, 2002, Pease et al., PCT Publication No. WO 01/64655, PCT Publication Date Sep. 7, 2001.

U.S. Appl. No. 10/220,139, filed Aug. 28, 2002, Pease et al., PCT Publication No. WO 01/64654, PCT Publication Date Sep. 7, 2001.

U.S. Appl. No. 10/203,025, filed Aug. 5, 2002, Pease et al., PCT Publication No. WO 01/64656, PCT Publication Date Sep. 7, 2001.

U.S. Appl. No. 10/203,549, filed Aug. 8, 2002, Pease et al., PCT Publication No. WO 01/64653, PCT Publication Date Sep. 7, 2001.

U.S. Appl. No. 10/069,019, filed Feb. 21, 2002, Thomas et al., PCT Publication No. WO 01/14375 A1, PCT Publication Date Mar. 1, 2001.

U.S. Appl. No. 10/239,790, filed Sep. 25, 2002, Thomas, PCT Publication No. WO 01/72717, PCT Publication Date Oct. 4, 2001.

U.S. Appl. No. 10/363,655, filed Mar. 4, 2003, Breault et al., PCT Publication No. WO 02/20512, PCT Publication Date Mar. 14, 2002.

U.S. Appl. No. 10/467,886, filed Aug. 13, 2003, Thomas, PCT Publication No. WO 02/066481 A1, PCT Publication Date Aug. 29, 2002.

Deady et al., "Reactions of some Quinazoline Compounds with Ethoxymethylenemalonic Acid Derivatives", J. Heterocyclic Chem., vol. 26, 1989, pp. 161–168.

El–Kerdawy et al.; "2,4–Bis(Substituted)–5–Nitropyrimidines of Expected Diuretic Action"; Egypt J. Chem. vol. 29, No. 1986, pp. 247–251.

Fiziol Akt Veshchestva, 1975, vol. 7, pp. 68–72.

Ghosh et al.; "2,4–Bis(arylamino)–5–methylprimidines as Antimicrobial Agents"; J. Med. Chem., 1967, vol. 10, No. 5, pp. 974–975.

Ghosh, "2,4–Bis(arylamino)–6–methylpyrimidines as an antimicrobial agents", Chemical Abstract No. 97712f, vol. 95, 1981, p. 648.

Schmidt et al.; "A Convenient Synthesis of 2–substituted 4–Amino–5–pyrimidinecarbonitriles"; J. Heterocycle Chem., 1997, vol. 24, No. 5, pp. 1305–1307.

Zimmermann et al., Phenylamino–Pyrimidine (PAP) Derivatives: A New Class of Potent and Selective Inhibitors of Protein Kinase C (PKC), Arch. Pharm. Pharm. Med. Chem., vol. 329, 1996, pp. 371–376.

* cited by examiner

PYRIMIDINE DERIVATIVES

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

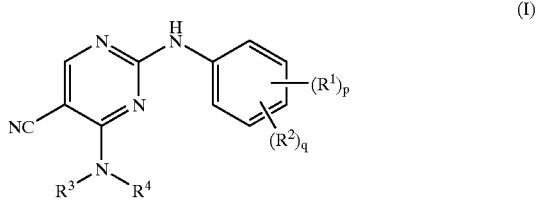

(I)

wherein:

$R^1$ is halo, nitro, cyano, hydroxy, amino, carboxy, carbamoyl, mercapto, $C_{1-6}$alkyl, $C_{2-6}$alkenyl or $C_{2-6}$alkynyl;

p is 0–4; wherein the values of $R^1$ may be the same or different;

$R^2$ is sulphamoyl or a group B-E-;

q is 0–2; wherein the values of $R^2$ maybe the same or different; and wherein p+q=1–5;

$R^3$ is hydrogen, $C_{1-6}$alkyl, $C_{2-6}$alkenyl, $C_{2-6}$alkynyl or $C_{3-8}$cycloalkyl; wherein $R^3$ may be optionally substituted on carbon by one or more M;

$R^4$ is $C_{1-6}$alkyl, $C_{2-6}$alkenyl, $C_{2-6}$alkynyl, $C_{3-8}$cycloalkyl or heterocyclyl; wherein $R^4$ may be optionally substituted by one or more M; wherein if said heterocyclyl contains an —NH— moiety that nitrogen may be optionally substituted by a group selected from Z;

or $R^3$ and $R^4$ together with the nitrogen to which they are attached form a heterocyclic ring optionally substituted on carbon by one or more M; wherein if said heterocyclic ring contains an —NH— moiety that nitrogen may be optionally substituted by a group selected from Q;

B is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, a heterocyclic group, phenyl$C_{1-6}$alkyl or (heterocyclic group)$C_{1-6}$alkyl; wherein B may be optionally substituted on carbon by one or more D; and wherein if said heterocyclic group contains an —NH— moiety that nitrogen may be optionally substituted by a group selected from G;

E is —C(O)—, —N($R^a$)C(O)—, —C(O)N($R^a$)—, —S(O)$_r$—, —SO$_2$N($R^a$)— or —N($R^a$)SO$_2$—; wherein $R^a$ is hydrogen or $C_{1-6}$alkyl optionally substituted by one or more D and r is 1–2;

D is independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl; wherein D may be optionally substituted on carbon by one or more V;

M is independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{3-8}$cycloalkyl, phenyl or a heterocyclic group; wherein M may be optionally substituted on carbon by one or more P; and wherein if said heterocyclic group contains an —NH— moiety that nitrogen may be optionally substituted by a group selected from T;

P, X and V are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and G, Q, T and Z are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)

carbamoyl, benzyl, benzyloxycarbonyl, benzoyl and phenyl-sulphonyl wherein G, Q and T may be independently optionally substituted on carbon by one or more X; or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" includes phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —$CH_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and or the S-oxides. Examples and suitable values of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Preferably a "heterocyclic group" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. In another aspect, preferably a "heterocyclic group" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. More preferably a "heterocyclic group" is tetrahydrofuryl, pyridyl, pyrrolidinonyl, morpholino, imidazolyl, piperidinyl or pyrrolidinyl. Particularly a "heterocyclic group" is tetrahydrofuryl or morpholino. In another aspect of the invention, particularly a "heterocyclic group" is morpholino, tetrahydrofuryl, piperidinyl, pyridyl, imidazolyl, piperazinyl, pyrrolidinyl, triazolyl, dioxanyl and dioxolanyl.

Where "$R^3$ and $R^4$ together with the nitrogen to which they are attached form a heterocyclic ring" said "heterocyclic ring" is a saturated, partially saturated or fully unsaturated, mono or bicyclic ring containing 4–12 atoms, one atom of which is the nitrogen atom to which $R^3$ and $R^4$ are attached to, and the other atoms are either all carbon atoms or they are carbon atoms and 1–3 heteroatoms chosen from nitrogen, sulphur or oxygen, wherein a —$CH_2$— group can optionally be replaced by a —C(O)—, a ring nitrogen atom may optionally bear a $C_{1-6}$alkyl group and form a quaternary compound or a ring nitrogen and/or a ring sulphur atom may be optionally oxidised to form an N- and/or an S-oxide. It will be appreciated that where $R^3$ and $R^4$ together with the nitrogen atom to which they are attached form a "heterocyclic ring" this nitrogen atom is not quaternised, i.e. a neutral compound is formed. Examples and suitable values of the term "heterocyclic group" are azetidinyl, morpholino, piperidyl, piperazinyl, pyrrolidinyl, thiomorpholino, pyrrolinyl, homopiperazinyl, pyrrolyl, pyrazolyl, pyrazolinyl, imidazolyl, imidazolinyl, imidazolidinyl, pyrazolidinyl and triazolyl. Preferably "heterocyclic group" is morpholino. In another aspect of the invention, preferably "heterocyclic group" is morpholino, piperidino, pyrrolidin-1-yl or piperazin-1-yl.

A "heterocyclyl" is a saturated mono or bicyclic ring containing 4–12 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form (the) S-oxide(s). Examples of the term "heterocyclyl" are morpholinyl, piperidyl, piperazinyl, thiazolidinyl, pyrrolidinyl, thiomorpholinyl, 1,1-dioxothiomorpholinyl, homopiperazinyl, tetrahydropyranyl, 2-pyrrolidone and 4-thiazolidone. In one aspect of the invention a "heterocyclyl" is a saturated monocyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form (the) S-oxide(s). In another aspect of the invention a "heterocyclyl" is tetrahydrofuryl.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include methoxy, ethoxy and propoxy. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$ alkylS(O)$_r$ wherein r is 1 to 2" include methylsulphinyl, ethylsulphinyl, mesyl and ethylsulphonyl. Examples of "$C_{1-6}$alkanoyl" include $C_{1-4}$alkanoyl, propionyl and acetyl. Examples of "N-$C_{1-6}$alkylamino" include methylamino and ethylamino. Examples of "N,N-($C_{1-6}$alkyl)$_2$amino" include di-N-methylamino, di-(N-ethyl) amino and N-ethyl-N-methylamino. Examples of "$C_{2-6}$alkenyl" are vinyl, allyl and 1-propenyl. Examples of "$C_{2-6}$alkynyl" are ethynyl, 1-propynyl and 2-propynyl. Examples of "N-($C_{1-6}$alkyl)sulphamoyl" are N-(methyl)sulphamoyl and N-(ethyl)sulphamoyl. Examples of "N-($C_{1-6}$alkyl)$_2$sulphamoyl" are N,N-(dimethyl)sulphamoyl and N-(methyl)-N-(ethyl)sulphamoyl. Examples of "N-($C_{1-6}$alkyl)carbamoyl" are N-($C_{1-4}$alkyl)carbamoyl, methylaminocarbonyl and ethylaminocarbonyl. Examples of "N,N-($C_{1-6}$alkyl)$_2$carbamoyl" are N,N-($C_{1-4}$alkyl)$_2$carbamoyl, dimethylaminocarbonyl and methylethylaminocarbonyl. Examples of "$C_{3-8}$cycloalkyl" are cyclopropyl, cyclobutyl, cyclopropyl and cyclohexyl. Examples of "(heterocyclic group)$C_{1-6}$alkyl" include pyridylmethyl, 3-morpholinopropyl and 2-pyrimid-2-ylethyl. Examples of "$C_{3-8}$cycloalkyl$C_{1-6}$alkyl" are cyclopropylethyl, cyclobutylmethyl, 2-cyclopropylpropyl and cyclohexylethyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl,benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazin-1-yl linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity.

It is also to be understood that certain compounds of the formula (I) can exist in solvated as well as unsolvated forms such as, for example, hydrated forms. It is to be understood that the invention encompasses all such solvated forms which possess CDK inhibitory activity.

Accordingly, in another aspect, the present invention provides a compound of formula (I):

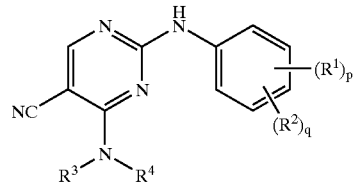

(I)

wherein:
$R^1$ is halo, nitro, cyano, hydroxy, amino, carboxy, carbamoyl, mercapto, $C_{1-6}$alkyl, $C_{2-6}$alkenyl or $C_{2-6}$alkynyl;
p is 0–4; wherein the values of $R^1$ may be the same or different;
$R^2$ is sulphamoyl or a group B-E-;
q is 0–2; wherein the values of $R^2$ maybe the same or different; and wherein p+q=1–5;
$R^3$ is hydrogen, $C_{1-6}$alkyl, $C_{2-6}$alkenyl, $C_{2-6}$alkynyl or $C_{3-8}$cycloalkyl; wherein said $C_{1-6}$alkyl, $C_{2-6}$alkenyl, $C_{2-6}$alkynyl or $C_{3-8}$cycloalkyl may be optionally substituted by one or more M; and
$R^4$ is $C_{1-6}$alkyl, $C_{2-6}$alkenyl, $C_{2-6}$alkynyl or $C_{3-8}$cycloalkyl; wherein said $C_{1-6}$alkyl, $C_{2-6}$alkenyl, $C_{2-6}$alkynyl or $C_{3-8}$cycloalkyl may be optionally substituted by one or more M;
or $R^3$ and $R^4$ together with the nitrogen to which they are attached form a heterocyclic ring optionally substituted on carbon by one or more M; wherein if said heterocyclic ring contains an —NH— moiety that nitrogen may be optionally substituted by a group selected from Q;
B is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, a heterocyclic group, phenyl$C_{1-6}$alkyl or (heterocyclic group)$C_{1-6}$alkyl; wherein said $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, heterocyclic group, phenyl$C_{1-6}$alkyl or (heterocyclic group)$C_{1-6}$alkyl are optionally substituted on carbon by one or more D; and wherein if said heterocyclic group contains an —NH— moiety that nitrogen may be optionally substituted by a group selected from G;
E is —C(O)—, —N($R^a$)C(O)—, —C(O)N($R^a$)—, —S(O)$_r$—, —SO$_2$N($R^a$)— or —N($R^a$)SO$_2$—; wherein $R^a$ is hydrogen or $C_{1-6}$alkyl optionally substituted by one or more D and r is 1–2;
D is independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$ alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$ alkyl)$_2$sulphamoyl; wherein D may be optionally substituted on carbon by a group selected from V;
M is independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl) amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl) sulphamoyl, N,N-($C_{1-6}$alkyl)$_2$sulphamoyl, $C_{3-8}$cycloalkyl, phenyl or a heterocyclic group; wherein M may be optionally substituted on carbon by a group selected from P; and wherein if said heterocyclic group contains an —NH— moiety that nitrogen may be optionally substituted by a group selected from T; and P and V are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

G, Q and T are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl; and or a pharmaceutically acceptable salt or an in vivo hydrolysable ester thereof.

Preferred values of $R^1$, $R^2$, $R^3$, $R^4$, p and q are as follows. Such values may be used where appropriate with any of the definitions, claims or embodiments defined hereinbefore or hereinafter.

Preferably $R^1$ is halo or $C_{1-2}$alkyl.

More preferably $R^1$ is fluoro, chloro or methyl.

Particularly $R^1$ is fluoro or chloro.

Preferably p is 0–2; wherein the values of $R^1$ may be the same or different.

More preferably p is 0 or 1.

In one aspect of the invention preferably p is 0.

In another aspect of the invention preferably p is 1.

In a further aspect of the invention preferably p is 2; wherein the values of $R^1$ may be the same or different.

Preferably when p is 1; $R^1$ is meta to the amino group in the aniline of formula (I).

Preferably $R^2$ is sulphamoyl or a group B-E-; wherein

B is selected from $C_{1-6}$alkyl, $C_{2-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl; wherein said $C_{1-6}$alkyl, $C_{2-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl are optionally substituted on carbon by one or more D; and wherein if said heterocyclic group contains an —NH— moiety that nitrogen may be optionally substituted by a group selected from G;

E is —N($R^a$)$SO_2$—; wherein $R^a$ is hydrogen;

D is independently selected from halo, hydroxy, $C_{1-6}$alkoxy or N-($C_{1-6}$alkyl)amino, N,N-($C_{1-6}$alkyl)$_2$amino; and G is $C_{1-4}$alkyl.

More preferably $R^2$ is sulphamoyl or a group B-E-; wherein

B is selected from $C_{1-6}$alkyl or (heterocyclic group)$C_{1-6}$alkyl; wherein said $C_{1-6}$alkyl or (heterocyclic group)$C_{1-6}$alkyl are optionally substituted on carbon by one or more D;

E is —N($R^a$)$SO_2$—; wherein $R^a$ is hydrogen;

D is independently selected from hydroxy or N-($C_{1-6}$alkyl)amino.

Particularly $R^2$ is selected from sulphamoyl, N-(3-hydroxy-2,2-dimethylpropyl)sulphamoyl, N-(3-(N-isopropylamino)propyl)sulphamoyl or N-(tetrahydrofur-2-ylmethyl)sulphamoyl.

In another aspect of the invention, preferably $R^2$ is sulphamoyl or a group B-E-;

B is selected from $C_{1-6}$alkyl, $C_{2-6}$alkenyl, $C_{2-6}$alkynyl or (heterocyclic group)$C_{1-6}$alkyl; wherein B may be optionally substituted on carbon by one or more D; and wherein if said heterocyclic group contains an —NH— moiety that nitrogen may be optionally substituted by a group selected from G;

E is —S(O)$_r$— or —N($R^a$)$SO_2$—; wherein $R^a$ is hydrogen or $C_{1-6}$alkyl and r is 2;

D is independently selected from halo, cyano, hydroxy, amino, $C_{1-6}$alkyl, $C_{1-6}$alkoxy, N-($C_{1-6}$alkyl)amino, N,N-($C_{1-6}$alkyl)$_2$amino, $C_{1-6}$alkanoylamino and $C_{1-6}$alkylS(O)$_a$ wherein a is 0 to 2; wherein D may be optionally substituted on carbon by a group selected from V;

V is selected from hydroxy and dimethylamino; and

G is selected from $C_{1-4}$alkyl.

In another aspect of the invention, more preferably $R^2$ is sulphamoyl or a group B-E-;

B is selected from methyl, ethyl, propyl, butyl, 2,2-dimethylpropyl, pentyl, allyl, 2-propynyl, pyrrolidin-2-ylmethyl, pyrid-3-ylmethyl, 1,4-dioxan-2-ylmethyl, pyrid-2-ylmethyl, 2-morpholinoethyl, 2-1,3,4-triaziol-2-ylethyl, 2-piperidinoethyl, 2-pyrid-2-ylethyl, 2-pyrid-4-ylethyl, 2-pyrrolidin-1-ylethyl, 2-imidazol-4-ylethyl, 3-imidazol-1-ylpropyl, 3-morpholinopropyl, 3-piperidinopropyl or tetrahydrofur-2-ylmethyl; wherein B may be optionally substituted on carbon by one or more D; and wherein if said heterocyclic group contains an —NH— moiety that nitrogen may be optionally substituted by a group selected from G;

E is —S(O)$_r$— or —N($R^a$)$SO_2$—; wherein $R^a$ is hydrogen or $C_{1-6}$alkyl and r is 2;

D is independently selected from fluoro, cyano, hydroxy, amino, methyl, methoxy, ethoxy, isopropylamino, dimethylamino, diethylamino, acetamido, ethylthio and mesyl; wherein D may be optionally substituted on carbon by a group selected from V;

V is selected from hydroxy and dimethylamino; and

G is selected from ethyl.

In another aspect of the invention, particularly $R^2$ is sulphamoyl, mesyl, ethylsulphonyl, 2-ethoxyethylsulphonyl, propylsulphonyl, 3-isopropylanminopropylsulphonyl, 4-isopropylaminobutylsulphonyl, N-(tetrahydrofur2-ylmethyl)sulphamoyl, N-(pyrid-3-ylmethyl)sulphamoyl, N-(pyrid-2-ylmethyl)sulphamoyl, N-(1,4-dioxan-2-ylmethyl)sulphamoyl, N-(methyl)sulphamoyl, N-(2-methoxyethyl)sulphamoyl, N-(2-ethylthioethyl)sulphamoyl, N-(2-morpholinoethyl)sulphamoyl, N-(2-piperidinoethyl)sulphamoyl, N-(2-pyrid-2-ylethyl)sulphamoyl, N-(2-pyrrolidin-1-ylethyl)sulphamoyl, N-(2-imidazol-4-ylethyl)sulphamoyl, N-(2-isopropylaminoethyl)sulphamoyl, N-(2-mesylethyl)sulphamoyl, N-[2-(2-hydroxyethoxy)ethyl]sulphamoyl, N-[2-(1-ethylpyrrolidin-2-yl)ethyl]sulphamoyl, N-(2-pyrid-2-ylethyl)sulphamoyl, N-(2-diethylaminoethyl)sulphamoyl, N-(2-pyrid-4-ylethyl)sulphamoyl, N-(2-acetamidoethyl)sulphamoyl, N-(2-dimethylaminoethyl)sulphamoyl, N-[2-(5-methyl-1,3,4-triazol-2-yl)ethyl]sulphamoyl, N-(2-hydroxyethyl)sulphamoyl, N-(2-cyanoethyl)sulphamoyl, N-(2-diethylaminoethyl)-N-(methyl)sulphamoyl, N-(2-methoxyethyl)-N-(methyl)sulphamoyl, N-(2,2,2-trifluoroethyl)sulphamoyl, N-(3-hydroxy-2,2-dimethylpropyl)sulphamoyl, N-($^3$-isopropylaminopropyl)sulphamoyl, N-(3-methoxypropyl)sulphamoyl, N-(3-imidazol-1-ylpropyl)sulphamoyl, N-(2-hydroxy-3-aminopropyl)sulphamoyl, N-(3-hydroxypropyl)sulphamoyl, N-(3-ethoxypropyl)sulphamoyl, N-[3-(2-dimethylaminoethyl)propyl]sulphamoyl, N-(3-morpholinopropyl)sulphamoyl, N-(2-hydroxypropyl)sulphamoyl, N-(2-hydroxy-3-piperidinopropyl)sulphamoyl, N-(3-piperidinopropyl)-N-(methyl)sulphamoyl, N-(2-hydroxybutyl)sulphamoyl, N-(pentyl)sulphamoyl, N-(5-hydroxypentyl)sulphamoyl, N-(allyl)sulphamoyl or N-(2-propynyl)sulphamoyl.

Preferably E is —NHSO$_2$—.

In another aspect of the invention, preferably E is —NHSO$_2$—, —N(Me)SO$_2$— or —SO$_2$—.

Preferably q is 0 or 1.

In one aspect of the invention preferably q is 0.

In another aspect of the invention preferably q is 1.

In a further aspect of the invention preferably q is 2; wherein the values of R$^2$ may be the same or different.

Preferably p+q=1 or 2.

More preferably p+q=1.

Preferably when q is 1; R$^2$ is meta or para to the amino group in the aniline of formula (I).

More preferably when q is 1; R$^2$ is para to the amino group in the aniline of formula (I).

Preferably R$^3$ is hydrogen, C$_{1-6}$alkyl, C$_{2-6}$alkenyl or C$_{2-6}$alkynyl; wherein said C$_{1-6}$alkyl, C$_{2-6}$alkenyl or C$_{2-6}$alkynyl may be optionally substituted by one or more M; and R$^4$ is C$_{1-6}$alkyl, C$_{2-6}$alkenyl or C$_{2-6}$alkynyl; wherein said C$_{1-6}$alkyl, C$_{2-6}$alkenyl C$_{2-6}$alkynyl may be optionally substituted by one or more M;

or R$^3$ and R$^4$ together with the nitrogen to which they are attached form a heterocyclic ring optionally substituted on carbon by one or more M; wherein if said heterocyclic ring contains an —NH— moiety that nitrogen may be optionally substituted by a group selected from More preferably R$^3$ is hydrogen or C$_{1-6}$alkyl; wherein said C$_{1-6}$alkyl may be optionally substituted by one or more M; and R$^4$ is C$_{1-6}$alkyl or C$_{2-6}$alkenyl; wherein said C$_{1-6}$alkyl or C$_{2-6}$alkenyl may be optionally substituted by one or more M;

or R$^3$ and R$^4$ together with the nitrogen to which they are attached form a heterocyclic ring; wherein M is independently selected from halo, cyano, C$_{1-6}$alkoxy, C$_{1-6}$alkoxycarbonyl or a heterocyclic group.

Particularly R$^3$ is hydrogen or C$_{1-4}$alkyl; and

R$^4$ is C$_{1-4}$alkyl or C$_{2-4}$alkenyl; wherein said C$_{1-4}$alkyl or C$_{2-4}$alkenyl may be optionally substituted by one or more M;

or R$^3$ and R$^4$ together with the nitrogen to -which they are attached form morpholino;

wherein

M is independently selected from fluoro, cyano, methoxy, ethoxy, ethoxycarbonyl or morpholino.

More particularly R$^3$ and R$^4$ together with the nitrogen to which they are attached form morpholino, i-butylamino, ethylamino, 2-fluoroethylamino, 3-ethoxypropylamino, butylamino, (N-methyl)allylamino, (N-methyl) ethoxycarbonylmethylamino, (N-methyl)-2-cyanoethylamino, N,N-diethylamino, (N-methyl)-2-methoxyethylamino, 2,2,2-trifluroethylamino, N,N-di-(2-cyanoethyl)amino or 3-morpholinopropylamino.

In another aspect of the invention, preferably R$^3$ is hydrogen or C$_{1-6}$alkyl; wherein R$^3$ may be optionally substituted by one or more M; and R$^4$ is C$_{1-6}$alkyl, C$_{2-6}$alkenyl, C$_{2-6}$alkynyl or C$_{3-8}$cycloalkyl; wherein R$^4$ may be optionally substituted by one or more M;

or R$^3$ and R$^4$ together with the nitrogen to which they are attached form a heterocyclic ring optionally substituted on carbon by one or more M; wherein if said heterocyclic ring contains an —NH— moiety that nitrogen may be optionally substituted by a group selected from Q;

M is independently selected from halo, cyano, hydroxy, C$_{1-6}$alkyl, C$_{1-6}$alkoxy, N,N-(C$_{1-6}$alkyl)$_2$amino, C$_{1-6}$alkoxycarbonyl, C$_{3-8}$cycloalkyl or a heterocyclic group; wherein M may be optionally substituted on carbon by a group selected from P;

P and X are independently selected from hydroxy and methoxy; and

Q is selected from C$_{1-4}$alkyl, C$_{1-4}$alkylsulphonyl or C$_{1-4}$alkoxycarbonyl; wherein Q may be optionally substituted on carbon by one or more X.

In another aspect of the invention, more preferably R$^3$ is hydrogen, methyl or ethyl; wherein R$^3$ may be optionally substituted by one or more M; and R$^4$ is methyl, ethyl, butyl, isobutyl, propyl, allyl, 2-propynyl, cyclopropyl or cyclohexyl; wherein R$^4$ may be optionally substituted by one or more M;

or R$^3$ and R$^4$ together with the nitrogen to which they are attached form morpholino, piperidino, pyrrolidin-1-yl or piperazin-1-yl optionally substituted on carbon by one or more M; wherein said piperazin-1-yl may be optionally substituted on nitrogen by a group selected from Q;

M is independently selected from fluoro, cyano, hydroxy, methyl, methoxy, ethoxy, dimethylamino, methoxycarbonyl, ethoxycarbonyl, butoxycarbonyl, cyclopropyl, tetrahydrofuryl, pyridyl, imidazolyl, dioxolanyl or morpholino; wherein M may be optionally substituted on carbon by a group selected from P;

P and X are independently selected from hydroxy and methoxy; and

Q is selected from methyl, ethyl, isopropyl, ethylsulphonyl or ethoxycarbonyl; wherein Q may be optionally substituted on carbon by one or more X.

Particularly R$^3$ and R$^4$ together with the nitrogen to which they are attached form isobutylamino, ethylamino, 2-fluoroethylamino, 3-ethoxypropylamino, butylamino, 2,2,2-trifluoroethylamino, 3-morpholinopropylamino, cyclopropylamino, cyclopropylmethylamino, cyclohexylamino, tetrahydrofur-2-ylmethylamino, 2-dimethylaminoethylamino, cyanomethylamino, pyrid-3-ylmethylamino, butoxycarbonylmethylamino, 2-(methoxycarbonyl)ethylamino, 2-hydroxyethylamino, methylamino, 2-propynylamino, 2-methoxyethylamino, 2-imidazol-4-ylethylamino, 2-(2-hydroxyethoxy) ethylamino, 2,3-dihydroxypropylamino, 2,2-dimethyldioxolan-4-ylmethylamino, propylamino, N-methyl-N-allylamino, N-methyl-N-ethoxycarbonylmethylamino, N-methyl-N-(2-cyanoethyl)amino, diethylamino, N-methyl-N-(2-methoxyethyl)amino, bis-(2-cyanoethyl)amino, N-ethyl-N-cyclohexylamino, N-methyl-N-(2,2,2-trifluoroethyl)amino, N-methyl-N-(2-propynyl)amino, morpholino, 2,6-dimethylmorpholino, 3,5-dimethylpiperidino, piperidino, 4-(2-methoxyethyl) piperazin-1-yl, 4-methylpiperazin-1-yl, 4-isopropylpiperazin-1-yl, 4-ethylsulphonylpiperazin-1-yl, 4-ethoxycarbonylpiperazin-1-yl, 4-(2-hydroxyethyl) piperazin-1-yl, and 3-hydroxypyrrolidin-1-yl.

Therefore in one aspect of the invention, there is provided a compound of formula (I) as depicted above wherein:

p is 0;

R$^2$ is sulphamoyl or a group B-E-; wherein

B is selected from C$_{1-6}$alkyl or (heterocyclic group)C$_{1-6}$alkyl; wherein said C$_{1-6}$alkyl or (heterocyclic group)C$_{1-6}$alkyl are optionally substituted on carbon by one or more D;

E is —N(R$^a$)SO$_2$—; wherein R$^a$ is hydrogen;

D is independently selected from hydroxy or N-(C$_{1-6}$alkyl)amino;

q is 1;

R$^3$ is hydrogen or C$_{1-6}$alkyl; wherein said C$_{1-6}$alkyl may be optionally substituted by one or more M; and R$^4$ is C$_{1-6}$alkyl or C$_{2-6}$alkenyl; wherein said C$_{1-6}$alkyl or C$_{2-6}$alkenyl may be optionally substituted by one or more M;

or $R^3$ and $R^4$ together with the nitrogen to which they are attached form a heterocyclic ring; wherein M is independently selected from halo, cyano, $C_{1-6}$alkoxy, $C_{1-6}$alkoxycarbonyl or a heterocyclic group;

or a pharmaceutically acceptable salt or an in vivo hydrolysable ester thereof.

Therefore in a further aspect of the invention, there is provided a compound of formula (I) as depicted above wherein:

p is 0;

$R^2$ is sulphamoyl, N-(3-hydroxy-2,2-dimethylpropyl)sulphamoyl, N-(3-(N-isopropylamino)propyl)sulphamoyl or N-(tetrahydrofur-2-ylmethyl)sulphamoyl;

q is 1;

$R^3$ and $R^4$ together with the nitrogen to which they are attached form morpholino, i-butylamino, ethylamino, 2-fluoroethylamino, 3-ethoxypropylamino, butylamino, (N-methyl)allylamino, (N-methyl)ethoxycarbonylmethylamino, (N-methyl)-2-cyanoethylamino, N,N-diethylamino, (N-methyl)-2-methoxyethylamino, 2,2,2-trifluroethylamino, N,N-di-(2-cyanoethyl)amino or 3-morpholinopropylamino;

or a pharmaceutically acceptable salt or an in vivo hydrolysable ester thereof.

Therefore in another further aspect of the invention, there is provided a compound of formula (I) (as depicted above); wherein:

p is 0;

In another aspect of the invention, preferably $R^2$ is sulphamoyl or a group B-E-;

B is selected from $C_{1-6}$alkyl, $C_{2-6}$alkenyl, $C_{2-6}$alkynyl or (heterocyclic group)$C_{1-6}$alkyl; wherein B may be optionally substituted on carbon by one or more D; and wherein if said heterocyclic group contains an —NH— moiety that nitrogen may be optionally substituted by a group selected from G;

E is —S(O)$_r$— or —N(R$^a$)SO$_2$—; wherein R$^a$ is hydrogen or $C_{1-6}$alkyl and r is 2;

D is independently selected from halo, cyano, hydroxy, amino, $C_{1-6}$alkyl, $C_{1-6}$alkoxy, N-($C_{1-6}$alkyl)amino, N,N-($C_{1-6}$alkyl)$_2$amino, $C_{1-6}$alkanoylamino and $C_{1-6}$alkylS(O)$_a$ wherein a is 0 to 2; wherein D may be optionally substituted on carbon by a group selected from V;

V is selected from hydroxy and dimethylamino;

G is selected from $C_{1-4}$alkyl;

q is 1;

$R^3$ is hydrogen or $C_{1-6}$alkyl; wherein $R^3$ may be optionally substituted by one or more M; and $R^4$ is $C_{1-6}$alkyl, $C_{2-6}$alkenyl, $C_{2-6}$alkynyl or $C_{3-8}$cycloalkyl; wherein $R^4$ may be optionally substituted by one or more M;

or $R^3$ and $R^4$ together with the nitrogen to which they are attached form a heterocyclic ring optionally substituted on carbon by one or more M; wherein if said heterocyclic ring contains an —NH— moiety that nitrogen may be optionally substituted by a group selected from Q;

M is independently selected from halo, cyano, hydroxy, $C_{1-6}$alkyl, $C_{1-6}$alkoxy, N,N-($C_{1-6}$alkyl)$_2$amino, $C_{1-6}$alkoxycarbonyl, $C_{3-8}$cycloalkyl or a heterocyclic group; wherein M may be optionally substituted on carbon by a group selected from P;

P and X are independently selected from hydroxy and methoxy;

Q is selected from $C_{1-4}$alkyl, $C_{1-4}$alkylsulphonyl or $C_{1-4}$alkoxycarbonyl; wherein G may be optionally substituted on carbon by one or more X;

or a pharmaceutically acceptable salt or an in vivo hydrolysable ester thereof.

Therefore in an additional further aspect of the invention, there is provided a compound of formula (I) (as depicted above); wherein:

p is 0;

$R^2$ is sulphamoyl or a group B-E-;

B is selected from methyl, ethyl, propyl, butyl, 2,2-dimethylpropyl, pentyl, allyl, 2-propynyl, pyrrolidin-2-ylmethyl, pyrid-3-ylmethyl, 1,4-dioxan-2-ylmethyl, pyrid-2-ylmethyl, 2-morpholinoethyl, 2-1,3,4-triaziol-2-ylethyl, 2-piperidinoethyl, 2-pyrid-2-ylethyl, 2-pyrid-4-ylethyl, 2-pyrrolidin-1-ylethyl, 2-imidazol-4-ylethyl, 3-imidazol-1-ylpropyl, 3-morpholinopropyl, 3-piperidinopropyl or tetrahydrofur-2-ylmethyl; wherein B may be optionally substituted on carbon by one or more D; and wherein if said heterocyclic group contains an —NH— moiety that nitrogen may be optionally substituted by a group selected from G;

E is —S(O)$_r$— or —N(R$^a$)SO$_2$—; wherein R$^a$ is hydrogen or $C_{1-6}$alkyl and r is 2;

D is independently selected from fluoro, cyano, hydroxy, amino, methyl, methoxy, ethoxy, isopropylamino, dimethylamino, diethylamino, acetamido, ethylthio and mesyl; wherein D may be optionally substituted on carbon by a group selected from V;

V is selected from hydroxy and dimethylamino;

G is selected from ethyl;

q is 1;

$R^3$ is hydrogen, methyl or ethyl; wherein $R^3$ may be optionally substituted by one or more M; and $R^4$ is methyl, ethyl, butyl, isobutyl, propyl, allyl, 2-propynyl, cyclopropyl or cyclohexyl; wherein $R^4$ may be optionally substituted by one or more M;

or $R^3$ and $R^4$ together with the nitrogen to which they are attached form morpholino, piperidino, pyrrolidin-1-yl or piperazin-1-yl optionally substituted on carbon by one or more M; wherein said piperazin-1-yl may be optionally substituted on nitrogen by a group selected from Q;

M is independently selected from fluoro, cyano, hydroxy, methyl, methoxy, ethoxy, dimethylamino, methoxycarbonyl, ethoxycarbonyl, butoxycarbonyl, cyclopropyl, tetrahydrofuryl, pyridyl, imidazolyl, dioxolanyl or morpholino; wherein M may be optionally substituted on carbon by a group selected from P;

P and X are independently selected from hydroxy and methoxy; and

Q is selected from methyl, ethyl, isopropyl, ethylsulphonyl or ethoxycarbonyl; wherein Q may be optionally substituted on carbon by one or more X;

or a pharmaceutically acceptable salt or an in vivo hydrolysable ester thereof.

Therefore in an another additional further aspect of the invention, there is provided a compound of formula (I) (as depicted above); wherein:

p is 0;

$R^2$ is sulphamoyl, mesyl, ethylsulphonyl, 2-ethoxyethylsulphonyl, propylsulphonyl, 3-isopropylaminopropylsulphonyl, 4-isopropylaminobutylsulphonyl, N-(tetrahydrofur-2-ylmethyl)sulphamoyl, N-(pyrid-3-ylmethyl)sulphamoyl, N-(pyrid-2-ylmethyl)sulphamoyl, N-(1,4-dioxan-2-ylmethyl)sulphamoyl, N-(methyl)sulphamoyl, N-(2-methoxyethyl)sulphamoyl, N-(2-ethylthioethyl)sulphamoyl, N-(2-morpholinoethyl)sulphamoyl, N-(2-piperidinoethyl)sulphamoyl, N-(2-pyrid-2-ylethyl)sulphamoyl, N-(2-pyrrolidin-1-ylethyl)sulphamoyl, N-(2-imidazol-4-ylethyl)sulphamoyl, N-(2-isopropylaminoethyl)sulphamoyl, N-(2-mesylethyl)sulphamoyl, N-[2-(2-hydroxyethoxy)ethyl]sulphamoyl, N-[2-(1-ethylpyrrolidin-2-yl)ethyl]

sulphamoyl, N-(2-pyrid-2-ylethyl)sulphamoyl, N-(2-diethylaminoethyl)sulphamoyl, N-(2-pyrid-4-ylethyl)sulphamoyl, N-(2-acetamidoethyl)sulphamoyl, N-(2-dimethylaminoethyl)sulphamoyl, N-[2-(5-methyl-1,3,4-triazol-2-yl)ethyl]sulphamoyl, N-(2-hydroxyethyl)sulphamoyl, N-(2-cyanoethyl)sulphamoyl, N-(2-diethylaminoethyl)-N-(methyl)sulphamoyl, N-(2-methoxyethyl)-N-(methyl)sulphamoyl, N-(2,2,2-trifluoroethyl)sulphamoyl, N-(3-hydroxy-2,2-dimethylpropyl)sulphamoyl, N-(3-isopropylaminopropyl)sulphamoyl, N-(3-methoxypropyl)sulphamoyl, N-(3-imidazol-1-ylpropyl)sulphamoyl, N-(2-hydroxy-3-aminopropyl)sulphamoyl, N-(3-hydroxypropyl)sulphamoyl, N-(3-ethoxypropyl)sulphamoyl, N-[3-(2-dimethylaminoethyl)propyl]sulphamoyl, N-(3-morpholinopropyl)sulphamoyl, N-(2-hydroxypropyl)sulphamoyl, N-(2-hydroxy-3-piperidinopropyl)sulphamoyl, N-(3-piperidinopropyl)-N-(methyl)sulphamoyl, N-(2-hydroxybutyl)sulphamoyl, N-(pentyl)sulphamoyl, N-(5-hydroxypentyl)sulphamoyl, N-(allyl)sulphamoyl or N-(2-propynyl)sulphamoyl;

q is 1 and $R^2$ is para to the amino group in the aniline of formula (I); and $R^3$ and $R^4$ together with the nitrogen to which they are attached form isobutylamino, ethylamino, 2-fluoroethylamino, 3-ethoxypropylamino, butylamino, 2,2,2-trifluoroethylamino, 3-morpholinopropylamino, cyclopropylamino, cyclopropylmethylamino, cyclohexylamino, tetrahydrofur-2-ylmethylamino, 2-dimethylaminoethylamino, cyanomethylamino, pyrid-3-ylmethylamino, butoxycarbonylmethylamino, 2-(methoxycarbonyl)ethylamino, 2-hydroxyethylamino, methylamino, 2-propynylamino, 2-methoxyethylamino, 2-imidazol-4-ylethylamino, 2-(2-hydroxyethoxy)ethylamino, 2,3-dihydroxypropylamino, 2,2-dimethyldioxolan-4-ylmethylamino, propylamino, N-methyl-N-allylamino, N-methyl-N-ethoxycarbonylmethylamino, N-methyl-N-(2-cyanoethyl)amino, diethylamino, N-methyl-N-(2-methoxyethyl)amino, bis-(2-cyanoethyl)amino, N-ethyl-N-cyclohexylamino, N-methyl-N-(2,2,2-trifluoroethyl)amino, N-methyl-N-(2-propynyl)amino, morpholino, 2,6-dimethylmorpholino, 3,5-dimethylpiperidino, piperidino, 4-(2-methoxyethyl)piperazin-1-yl, 4-methylpiperazin-1-yl, 4-isopropylpiperazin-1-yl, 4-ethylsulphonylpiperazin-1-yl, 4-ethoxycarbonylpiperazin-1-yl, 4-(2-hydroxyethyl)piperazin-1-yl, and 3-hydroxypyrrolidin-1-yl;

or a pharmaceutically acceptable salt or an in vivo hydrolysable ester thereof.

In another aspect of the invention, preferred compounds of the invention are any one of Examples 1–17 or a pharmaceutically acceptable salt or an in vivo hydrolysable ester thereof.

In another aspect of the invention, preferred compounds of the invention are any one of the Examples or a pharmaceutically acceptable salt or an in vivo hydrolysable ester thereof.

In an additional aspect of the invention, preferred compounds of the invention are Examples 24, 38, 58, 59, 60, 63, 67, 73, 95 or 126 or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, $R^4$, p and q are, unless otherwise specified, as defined in formula (I)) comprises of:

a) reaction of a pyrimidine of formula (II):

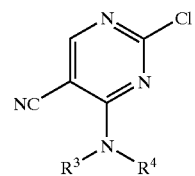

(II)

wherein L is a displaceable group; with an aniline of formula (III):

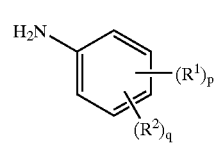

(III)

b) reacting a pyrimidine of formula (IV):

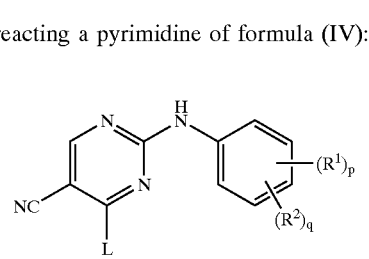

(IV)

wherein L is a displaceable group; with an amine of formula (V):

$R^3R^4NH$ (V)

or c) reacting a compound of formula (VI):

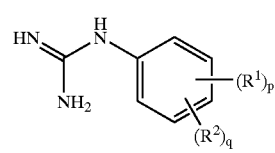

(VI)

with a compound of formula (VII):

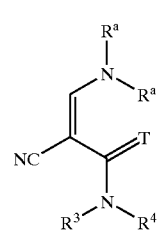

(VII)

wherein T is O or S; $R^a$ may be the same or different and is selected from $C_{1-6}$alkyl;

d) for compounds of formula (I) where $R^2$ is sulphamoyl or a group B-E- and E is —NHSO$_2$—;
reacting a pyrimidine of formula (VIII):

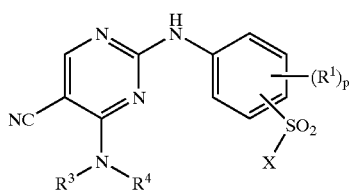
(VIII)

wherein X is a displaceable group; with an amine of formula (IX):

B—NH$_2$ (IX)

e) by converting a compound of formula (X):

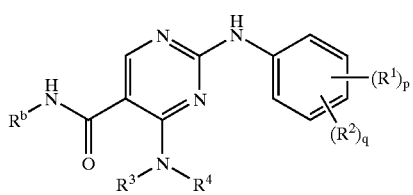
(X)

wherein $R^b$ is hydrogen or t-butyl; into a compound of formula (I); and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno, (optionally substituted) aryloxy or sulphonyloxy group, for example a chloro, bromo, phenoxy, methanesulphonyloxy or toluene-4-sulphonyloxy group.

X is a displaceable group, suitable values for X are for example, a halogeno group, for example a fluoro, chloro or bromo group. Preferably X is fluoro.

Preferably T is S.

specific reaction conditions for the above reactions are as follows.

a) and b) Pyrimidines of formula (II) and anilines of formula (III) and pyrimidines of formula (IV) and amines of formula (V) may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) and (IV) and anilines of formula (III) and amines of formula (V) are commercially available compounds, or they are known in the literature, or they are prepared by standard processes known in the art.

c) Compounds of formula (VI) and compounds of formula (VII) are reacted together in a suitable solvent such as N-methylpyrrolidinone or butanol at a temperature in the range of 100–200° C., preferably in the range of 150–170° C. The reaction is preferably conducted in the presence of a suitable base such as, for example, sodium methoxide or potassium carbonate.

Compounds of formula (VI) and (VII) are commercially available compounds, or they are known in the literature, or they are prepared by standard processes known in the art.

d) Compounds of formula (VIII) and compounds of formula (IX) may be reacted together in the presence of a base for example an inorganic base such as caesium carbonate in the presence of an inert solvent such as toluene or tetrahydrofuran, or in the presence of an organic base such as excess (IX) and at a temperature in the range of 25 to 80° C.

Compounds of formula (VIII) wherein X is fluoro may be prepared according to the following scheme:

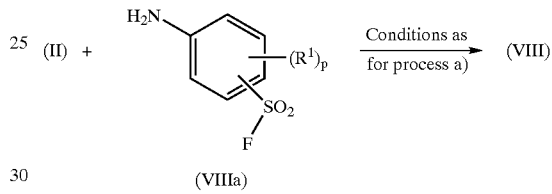
(VIIIa)

Compounds of formula (VIIIa) and (IX) are commercially available compounds, or they are known in the literature, or they are prepared by standard processes known in the art.

e) Compounds of formula (X) may be converted into compounds of formula (I) under standard conditions, for example in the presence of trifluoroacetic anhydride (where $R^b$ is hydrogen) or thionyl chloride at a temperature in the range of 25 to 100° C.

Compounds of formula (X) may be prepared according to scheme 1 or scheme 2:

Scheme 1

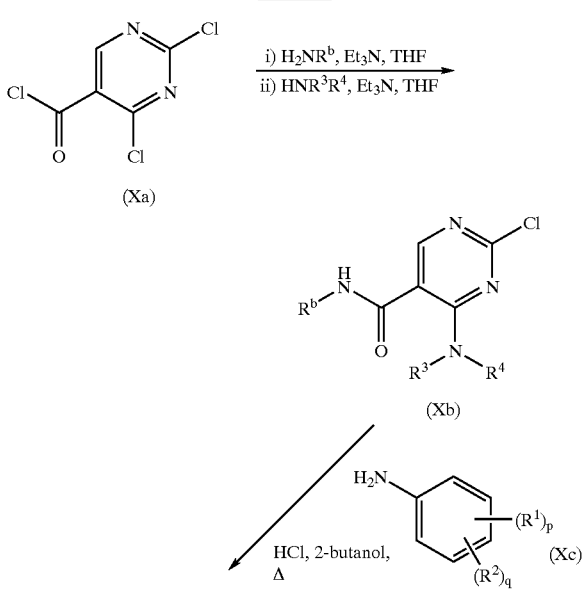

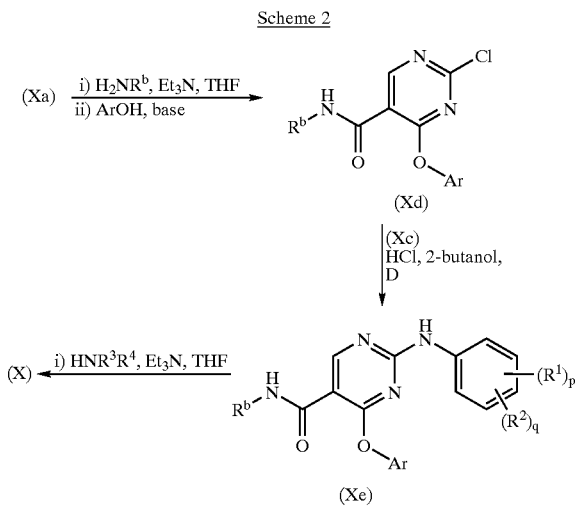

wherein Ar is optionally substituted aryl, for example phenyl.

Compounds of formula (Xa) and (Xc) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:—

Assay

The following abbreviations have been used:—
HEPES is N-[2-Hydroxyethyl]piperazine-N'-[2-ethanesulfonic acid]
DTT is Dithiothreitol
PMSF is Phenylmethylsulphonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 μl of CDK2/Cyclin E partially-purified enzyme (amount dependent on enzyme activity)

diluted in 25 μl incubation buffer was added to each well then 20 μl of GST-Rb/ATP/ATP33 mixture (containing 0.5 μg GST-Rb and 0.2 μM ATP and 0. 14 μCi [γ-33-P]-Adenosine Triphosphate in incubation buffer), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 m M EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM $MnCl_2$, 1 mM DTT, 100 μM Sodium vanadate, 100 μM NaF, 10 mM Sodium Glycerophosphate, BSA (1 mg/ml final).
Test Substrate In this assay only part of the retinoblastoma protein (Science 1987 Mar. 13; 235 (4794): 1394–1399; Lee W. H., Bookstein R., Hong F., Young L. J., Shew J. Y., Lee E. Y.) was used, fused to a GST tag. PCR of retinoblastoma gene encoding amino acids 379–928 (obtained from retinoblastoma plasmid ATCC pLRbRNL) was performed, and the sequence cloned into pQEX 2T fusion vector (Smith D. B. and Johnson, K. S. Gene 67, 31 (1988); which contained a tac promoter for inducible expression, internal lac $I^q$ gene for use in any E. Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E. Coli (BL21 (DE3) pLysS cells) using standard inducible expression techniques, and purified as follows.

E. coli paste was resuspended in 10 ml/g of NETN buffer (50 mM Tris pH 7.5, 120 mM NaCl, 1 mM EDTA, 0.5% v/v NP-40, 1 mM PMSF, 1 ug/mnl leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM $MgCl_2$, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).
CDK2 and Cyclin E The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number: V1392-20). CDK2 and cyclin E were then dually expressed [using a standard virus Baculogold co-infection technique] in the insect SF21 cell system (Spodoptera Frugiperda cells derived from ovarian tissue of the Fall Army Worm—commercially available).

Example Production of Cyclin E/CDK2

The following Example provides details of the production of Cyclin E/CDK2 in SF21 cells (in TC100+10% FBS (TCS)+0.2% Pluronic) having dual infection MOI 3 for each virus of Cyclin E & CDK2.

SF21 cells grown in a roller bottle culture to 2.33×10⁶ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Litres of culture was harvested. The total cell count at harvest was 1.58×10E6 cells/ml. (99% viable). The cells were spun out at 2500 rpm, 30 mins., 4° C. in Heraeus Omnifuge 2.0 RS in 250 ml. lots. The supernatant was discarded.
Partial Co-Purification of Cdk2 and Cyclin E Sf21 cells were resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0–1M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK4 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 250 μM to 1 nM.

When tested in the above in-vitro assay the CDK2 inhibitory activity of Example 1 was measured as $IC_{50}$=0.148 μM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R.(1989) Status of the NCI preclinical antitumour drug discovery screen. Prin. Prac Oncol 10:1–12). Thus, the following details are provided of measuring inhibition of cell growth:—

Cells were plated in appropriate medium in a volume of 100□l in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% $CO_2$) for three days.

At the end of three days TCA was added to the plates to a final concentration of 16% (v/v). Plates were then incubated at 4° C. for 1 hour, the supernatant removed and the plates washed in tap water. After drying, 100□l SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is provided a pharmaceutical composition which comprises a compound of the formula (a), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophospharnide; antimetabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:

a) a compound of formula (I), or a pharmaceutically acceptable salt or in vivo hydrolysable ester thereof, in a first unit dosage form;

b) a pharmaceutical agent for treating malignant conditions that is known to cause hair loss; in a second unit dosage form; and c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:
(i) other cell cycle inhibitory agents that work by the same or different mechanisms from those defined hereinbefore;
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and
(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan).

According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:
(i) temperatures are given in degrees Celsius (° C.); operations were carried out at room or ambient temperature, that is, at a temperature in the range of 18–25° C.;
(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;
(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is (MH)$^+$;
(xi) unless stated otherwise compounds containing an asymmetrically substituted carbon and/or sulphur atom have not been resolved;
(xii) where a synthesis is described as being analogous to that described in a previous example the amounts used are the millimolar ratio equivalents to those used in the previous example;,
(xvi) the following abbreviations have been used:

| THF | tetrahydrofuran; |
|---|---|
| SM | starting material; |
| NMP | N-methylpyrrolidinone; |

| | -continued | |
|---|---|---|
| DCM | dichloromethane; and | |
| DMSO | dimethylsulphoxide. | |

Example 1

5-Cyano-4-morpholino-2-{4-[N-(3-isopropylaminopropyl)sulphamoyl]anilino}pyrimidine 2-Chloro-5-cyano-4-morpholinopyrimidine (Method 55; 425 mg, 1.90 mmol), 4-[N-(3-isopropylaminopropyl) sulphamoyl]aniline (Method 1; 514 mg, 1.90 mmol) and 1M ethereal hydrogen chloride (189□l, 3.79 mmol) in 2-butanol (2 ml) was heated at 95° C. for 15 hours. The mixture was allowed to cool, silica was added and the volatiles were evaporated. The residue was purified by chromatography eluting with DCM/methanolic ammonia (100:0) increasing in polarity to (92:8) and the product was recrystallized from methanol to give the title compound (164 mg, 19%). NMR: 0.89 (d, 6H), 1.44 (m, 2H), 2.40 (t, 2H), 2.56 (m, 1H), 2.76 (t, 2H), 3.68–3.74 (m, 4H), 3.83–3.90 (m, 4H), 7.69 (d, 2H), 7.83 (d, 2), 8.49 (s, 1H), m/z: 460.

Examples 2–11

Following the procedure of Example 1 using 4-[N-(3-isopropylaminopropyl)sulphamoyl]aniline (Method 1) and the appropriate 4-substituted pyrimidine starting material the following compounds were prepared.

| Ex | Compound Name | NMR | m/z | SM |
|---|---|---|---|---|
| 2 | 5-Cyano-4-(2-methylpropyl-amino)-2-{4-[N-(3-isopropylaminopropyl)sulphamoyl]anilino}pyrimidine | 0.86 (d, 6H), 0.90 (d, 6H), 1.44 (m, 2H), 1.99 (m, 1H), 2.40 (t, 2H), 2.56 (m, 1H), 2.76 (t, 2H), 3.23 (t, 2H), 7.66 (d, 2H), 7.92 (d, 2H), 7.97 (m, 1H), 8.37 (s, 1H), 10.13 (brs, 1H) | 446 | Meth 57 |
| 3 | 5-Cyano-4-ethylamino-2-{4-[N-(3-isopropylaminopropyl)sulphamoyl]anilino}pyrimidine | 0.89 (d, 6H), 1.17 (t, 3H), 1.45 (m, 2H), 2.41 (t, 2H), 2.56 (m, 1H), 2.76 (t, 2H), 3.45 (m, 2H), 7.67 (d, 2H), 7.84 (brt, 1H), 7.94 (d, 2H), 8.38 (s, 1H), 10.13 (brs, 1H) | 418 | Meth 56 |
| 4 | 5-Cyano-4-(2-fluoroethyl-amino)-2-{4-[N-(3-isopropylaminopropyl)sulphamoyl]anilino}pyrimidine | 0.90 (d, 6H), 1.44 (m, 2H), 2.41 (t, 2H), 2.57 (m, 1H), 2.75 (t, 2H), 3.69 (m, 1H), 3.78 (m, 1H), 4.53 (t, 1H), 4.69 (t, 1H), 7.68 (d, 2H), 7.88 (d, 2H), 7.98 (m, 1H), 8.42 (s, 1H), 10.18 (brs, 1H) | 436 | Meth 58 |
| 5 | 5-Cyano-4-(3-ethoxypropyl-amino)-2-{4-[N-(3-isopropylaminopropyl)sulphamoyl]anilino}pyrimidine | 0.89 (d, 6H), 1.09 (t, 3H), 1.44 (m, 2H), 1.82 (m, 2H), 2.41 (t, 2H), 2.56 (m, 1H), 2.76 (t, 2H), 3.36–3.53 (m, 6H), 7.67 (d, 2H), 7.80 (t, 1H), 7.94 (d, 2H), 8.38 (s, 1H), 10.15 (brs, 1H) | 476 | Meth 59 |
| 6 | 5-Cyano-4-butylamino-2-{4-[N-(3-isopropylaminopropyl)sulphamoyl]anilino}pyrimidine | 0.86–0.94 (m, 9H), 1.34 (m, 2H), 1.46 (m, 2H), 1.57 (m, 2H), 2.41 (t, 2H), 2.58 (m, 1H), 2.75 (t, 2H), 3.41 (m, 2H), 7.66 (d, 2H), 7.89 (t, 1H), 7.93 (d, 2H), 8.37 (s, 1H), 10.14 (brs, 1H) | 446 | Meth 60 |
| 7 | 5-Cyano-4-(N-(methyl)-allylamino)-2-{4-[N-(3-isopropylaminopropyl)sulphamoyl]anilino}pyrimidine | 0.89 (d, 6H), 1.44 (m, 2H), 2.41 (t, 2H), 2.57 (m, 1H), 2.76 (t, 2H), 3.25 (s, 3H), 4.34 (d, 2H), 5.19 (m, 2H), 5.90 (m, 1H), 7.68 (d, 2H), 7.86 (d, 2H), 8.44 (s, 1H), 10.18 (brs, 1H) | 444 | Meth 61 |
| 8 | 5-Cyano-4-(N-(methyl)-ethoxycarbonylmethylamino)-2-{4-[N-(3-isopropylaminopropyl)sulphamoyl]anilino}pyrimidine | 0.89 (d, 6H), 1.14 (t, 3H), 1.45 (m, 2H), 2.41 (t, 2H), 2.58 (m, 1H), 2.76 (t, 2H), 3.38 (s, 3H), 4.09 (q, 2H), 4.50 (s, 2H), 7.66 (d, 2H), 7.79 (d, 2H), 8.49 (s, 1H), 10.24 (brs, 1H) | 490 | Meth 62 |
| 9 | 5-Cyano-4-(N-(methyl)-2-cyanoethylamino)-2-{4-[N-(3-isopropylaminopropyl)sulphamoyl]anilino}pyrimidine | 0.89 (d, 6H), 1.44 (m, 2H), 2.41 (t, 2H), 2.58 (m, 1H), 2.77 (t, 2H), 2.93 (t, 2H), 3.38 (s, 3H), 3.99 (t, 2H), 7.70 (d, 2H), 7.85 (d, 2H), 8.49 (s, 1H), 10.24 (brs, 1H) | 457 | Meth 63 |
| 10 | 5-Cyano-4-diethylamino-2-{4-[N-(3-isopropylamino-propyl)sulphamoyl]anilino}pyrimidine | 0.93 (d, 6H), 1.21 (t, 6H), 1.51 (m, 2H), 2.49 (m, 2H), 2.65–2.80 (m, 3H), 3.69 (m, 4H), 7.69 (d, 2H), 7.88 (d, 2H), 8.40 (s, 1H), 10.14 (brs, 1H) | 446 | Meth 64 |
| 11 | 5-Cyano-4-(N-(methyl)-2-methoxyethylamino)-2-{4-[N-(3-isopropylaminopropyl)sulphamoyl]anilino}pyrimidine | 0.89 (d, 6H), 1.46 (m, 2H), 2.41 (t, 2H), 2.56 (m, 1H), 2.76 (t, 2H), 3.25 (s, 3H), 3.31 (s, 3H), 3.59 (t, 2H), 3.90 (t, 2H), 7.68 (d, 2H), 7.86 (d, 2H), 8.42 (s, 1H), 10.17 (brs, 1H) | 462 | Meth 65 |

Example 12

5-Cyano-4-(3-morpholinopropylamino)-2-{4-[N-(tetrahydrofur-2-ylmethyl)sulphamoyl]anilino)pyrimidine 2Chloro-5-cyano-4-(3-morpholinopropylamino)pyrimidine (Method 66; 525 mg, 1.87 mmol), 4-[N-(tetrahydrofur-2-ylmethyl)sulphamoyl]aniline (Method 2; 430 mg, 1.68 mmol) and 1M ethereal hydrogen chloride (1.87 ml, 1.87 mmol) in 2-butanol (3 ml) was heated at 90° C. for 3 hours. The mixture was allowed to cool, the resulting precipitate was collected by filtration and was washed with ethyl acetate. The crude solid was purified by chromatography eluting with DCM/methanolic ammonia/ (100:0) increasing in polarity to (97:3). The product was recrystallized from methanol to give the title compound (111 mg).

NMR: 1.50 (m, 1H), 1.67–1.88 (m, 5H), 2.28–2.40 (m, 6H), 2.73 (t, 2H), 3.48 (m, 2H), 3.51–3.60 (m, 5H), 3.67 (m, 1H), 3.77 (m, 1H), 7.50 (t, 1H), 7.69 (d, 2H), 7.91 (d, 2H), 7.93 (s, 1H), 8.38 (s, 1H), 10.13 (brs, 1H); m/z: 502.

Examples 13–19

Following the procedure of Example 12 using 4-[N-(tetrahydrofur-2-ylmethyl)sulphamoyl]aniline (Method 2) and the appropriate 4-substituted pyrimidine starting material the following compounds were prepared.

| Ex | Compound Name | NMR | m/z | SM |
|---|---|---|---|---|
| 13 | 5-Cyano-4-(diethylamino)-2-{4-[N-(tetrahydrofur-2-ylmethyl)sulphamoyl]anilino}pyrimidine | 1.24 (t, 6H), 1.52 (m, 1H), 1.70–1.90 (m, 3H), 2.75 (t, 2H), 3.56 (m, 1H), 3.60–3.84 (m, 6H), 7.56 (t, 1H), 7.71 (d, 2H), 7.88 (d, 2H), 8.43 (s, 1H), 10.18 (s, 1H) | 431 | Meth 64 |
| 14 | 5-Cyano-2-{4-[N-(tetrahydrofur-2-ylmethyl)sulphamoyl]anilino}-4-(2-methylpropylamino)pyrimidine | 1.52 (m, 1H), 1.70–1.90 (m, 3H), 2.00 (m, 1H), 3.24 (t, 2H), 3.58 (m, 1H), 3.67 (m, 1H), 3.78 (q, 1H), 7.58 (t, 1H), 7.70 (d, 2H), 7.95 (d, 2H), 8.02 (brt, 1H), 8.40 (s, 1H), 10.18 (s, 1H) | 431 | Meth 57 |
| 15 | 5-Cyano-4-[N-(methyl)allylamino]-2-{4-[N-(tetrahydrofur-2-ylmethyl)sulphamoyl]anilino}pyrimidine | 1.52 (m, 1H), 1.65–1.90 (m, 3H), 2.74 (t, 2H), 3.28 (s, 3H), 3.58 (m, 1H), 3.67 (m, 1H), 3.79 (q, 1H), 4.35 (d, 2H), 5.24 (m, 2H), 5.92 (m, 1H), 7.57 (t, 1H), 7.70 (d, 2H), 7.89 (d, 2H), 8.48 (s, 1H), 10.22 (s, 1H) | 429 | Meth 61 |
| 16 | 5-Cyano-4-(2-fluoroethylamino)-2-{4-[N-(tetrahydrofur-2-ylmethyl)sulphamoyl]anilino}pyrimidine | 1.50 (m, 1H), 1.74 (m, 2H), 1.80 (m, 1H), 2.76 (m, 2H), 3.54 (m, 1H), 3.68 (m, 2H), 3.78 (m, 2H), 4.55 (t, 1H), 4.68 (t, 1H), 7.51 (t, 1H), 7.70 (d, 2H), 7.89 (d, 2H), 7.99 (t, 1H), 8.42 (s, 1H), 10.19 (s, 1H) | 421 | Meth 58 |
| 17 | 5-Cyano-4-[N-(methyl)-2-cyanoethylamino]-2-{4-[N-(tetrahydrofur-2-ylmethyl)sulphamoyl]anilino}pyrimidine | 1.52 (m, 1H), 1.70–1.90 (m, 3H), 2.78 (t, 2H), 2.94 (t, 2H), 3.38 (s, 3H), 3.57 (q, 1H), 3.68 (q, 1H), 3.78 (q, 1H), 4.00 (t, 2H), 7.54 (t, 1H), 7.74 (d, 2H), 7.85 (d, 2H), 8.50 (s, 1H), 10.25 (s, 1H) | 442 | Meth 63 |
| 18 | 5-Cyano-4-[2-(dimethylamino)ethylamino]-2-{4-[N-(tetrahydrofur-2-ylmethyl)sulphamoyl]anilino}pyrimidine | 1.52 (m, 1H), 1.70–1.90 (m, 3H), 2.20 (s, 6H), 2.48 (m, 2H), 2.75 (t, 2H), 3.54 (m, 3H), 3.68 (q, 1H), 3.79 (quin, 1H), 7.52 (t, 1H), 7.67 (m, 3H), 7.93 (d, 2H), 8.40 (s, 1H), 10.16 (s, 1H) | 446 | Meth 97 |
| 19 | 5-Cyano-4-(cyanomethylamino)-2-{4-[N-(tetrahydrofur-2-ylmethyl)sulphamoyl]anilino}pyrimidine | 1.50 (m, 1H), 1.68–1.88 (m, 3H), 2.74 (t, 2H), 3.54 (m, 1H), 3.65 (m, 1H), 3.78 (quintet, 1H), 4.38 (d, 2H), 7.52 (t, 1H), 7.71 (d, 2H), 7.94 (d, 2H), 8.45 (t, 1H), 8.52 (s, 1H), 10.39 (s, 1H) | 414 | Meth 100 |

Examples 20–28

Following the procedure of Example 12 using 4-[N-(2-methoxyethyl)sulphamoyl]aniline (Method 5) and the appropriate 4-substituted pyrimidine starting material the following compounds were prepared.

| Ex | Compound Name | NMR | m/z | SM |
|---|---|---|---|---|
| 20 | 5-Cyano-4-[N-(methyl)-2-methoxyethylamino]-2-{4-[N-(2-methoxyethyl)sulphamoyl]anilino}pyrimidine | 2.89 (q, 2H), 3.15 (s, 3H), 3.30 (2 × s, m, 8H), 3.60 (t, 2H), 3.92 (t, 2H), 7.52 (t, 1H), 7.72 (d, 2H), 7.87 (d, 2H), 8.45 (s, 1H), 10.18 (s, 1H) | 421 | Meth 65 |
| 21 | 5-Cyano-4-(2,6-dimethylmorpholino)-2-{4-[N-(2-methoxyethyl)sulphamoyl]anilino}pyrimidine (cis and trans isomers) | 1.15 (d, 6H), 2.74–2.94 (q and m, 4H), 3.18 (s, 3H), 3.29 (m, 2H), 3.65 (m, 2H cis and trans isomers), 3.98 (dd) and 4.08 (m) (cis and trans isomers, 1H), 4.52 (d, 2H), 7.53 (brt, 1H), 7.72 (d, 2H), 7.84 (d, 2H), 8.51 (s, 1H), 10.23 (s, 1H) | 447 | Meth 98 |
| 22 | 5-Cyano-4-(cis-2,6-dimethylmorpholino)-2-{4-[N-(2-methoxyethyl)sulphamoyl]anilino}pyrimidine | 1.15 (d, 6H), 2.74 (m 2H), 2.88 (q, 2H), 3.18 (s, 3H), 3.29 (m, 2H), 3.65 (m, 2H), 4.52 (d, 2H), 7.53 (brt, 1H), 7.72 (d, 2H), 7.84 (d, 2H), 8.51 (s, 1H), 10.24 (s, 1H) | 447 | Meth 99 |
| 23[1] | 5-Cyano-4-(3,5-dimethylpiperidino)-2-{4-[N-(2-methoxyethyl)sulphamoyl]anilino}pyrimidine | 0.89 (7H, d + m), 1.68 (m, 2H), 1.81 (brd, 1H), 2.61 (t, 2H), 2.88 (m, 2H), 3.15 (s, 3H), 3.29 (m, 2H), 4.60 (dxq, 2H), 7.54 (t, 1H), 7.71 (d, 2H), 7.85 (d, 2H), 8.44 (s, 1H), 10.18 (s, 1H) | 445 | Meth 101 |
| 24 | 5-Cyano-4-ethylamino-2-{4-[N-(2-methoxyethyl)sulphamoyl]anilino}pyrimidine | 1.19 (t, 3H), 2.88 (m, 2H), 3.15 (s, 3H), 3.28 (m, 2H), 3.45 (m, 2H), 7.50 (t, 1H), 7.70 (d, 2H), 7.86 (t, 1H), 7.92 (d, 2H), 8.49 (s, 1H), 10.14 (s, 1H) | 377 | Meth 56 |
| 25 | 5-Cyano-4-[4-(2-methoxyethyl)piperazin-1-yl]-2-{4-[N-(2-methoxyethyl)sulphamoyl]anilino}pyrimidine | 2.56 (m, 4H), 2.50 (m, 2H), 2.89 (m, 2H), 3.15 (s, 3H), 3.23 (s, 3H), 3.27 (m, 2H), 3.46 (m, 2H), 3.86 (m, 4H), 7.51 (t, 1H), 7.72 (d, 2H), 7.84 (d, 2H), 8.50 (s, 1H), 10.21 (s, 1H) | 476 | Meth 102 |
| 26 | 5-Cyano-2-{4-[N-(2-methoxyethyl)sulphamoyl]anilino}-4-(4-methyl-piperazin-1-yl)pyrimidine | 2.20 (s, 3H), 2.43 (m, 4H), 2.89 (m, 2H), 3.15 (s, 3H), 3.28 (m, 2H), 3.87 (m, 4H), 7.50 (t, 1H), 7.72 (d, 2H), 7.84 (d, 2H), 8.49 (s, 1H), 10.21 (s, 1H) | 432 | Meth 103 |
| 27 | 5-Cyano-4-(4-isopropylpiperazin-1-yl)-2-{4-[N-(2-methoxyethyl)sulphamoyl]anilino}pyrimidine | 0.99 (d, 6H), 2.56 (m, 4H), 2.69 (m, 1H), 2.89 (q, 2H), 3.17 (s, 3H), 3.29 (m, 2H), 3.87 (m, 4H), 7.52 (t, 1H), 7.72 (d, 2H), 7.84 (d, 2H), 8.48 (s, 1H), 10.21 (s, 1H) | 460 | Meth 104 |
| 28 | 5-Cyano-4-[4-(ethylsulphonyl)piperazin-1-yl]-2-{4-[N-(2-methoxyethyl)sulphamoyl]anilino}pyrimidine | 1.21 (t, 3H), 2.89 (q, 2H), 3.12 (q, 2H), 3.17 (s, 3H), 3.29 (m, 2H), 3.36 (t, 4H), 3.94 (t, 4H), 7.51 (t, 1H), 7.74 (d, 2H), 7.85 (d, 2H), 8.54 (s, 1H), 10.30 (s, 1H) | 510 | Meth 105 |

[1] cis and trans isomers in 80:20 mixture (by NMR).

Examples 29–34

Following the procedure of Example 12 using 4-[N-(3-methoxypropyl)sulphamoyl]aniline (Method 4) and the appropriate 4-substituted pyrimidine starting material the following compounds were prepared.

| Ex | Compound Name | NMR | m/z | SM |
|---|---|---|---|---|
| 29 | 5-Cyano-4-(4-ethoxycarbonylpiperazin-1-yl)-2-{4-[N-(3-methoxypropyl) | 1.22 (t, 3H), 1.59 (m, 2H), 2.78 (m, 2H), 3.16 (s, 3H), 3.28 (t, 2H), 3.58 (m, 4H), 3.91 (m, 4H), 4.08 (q, 2H), 7.40 (t, 1H), 7.74 (d, 2H), 7.88 (d, 2H), | 504 | Meth 106 |

-continued

| Ex | Compound Name | NMR | m/z | SM |
|----|---------------|-----|-----|-----|
|    | sulphamoyl]anilino} pyrimidine | 8.54 (s, 1H), 10.29 (s, 1H) | | |
| 30 | 5-Cyano-2-{4-[N-(3-methoxypropyl)sulphamoyl]anilino}-4-methylamino pyrimidine | 1.60 (m, 2H), 2.78 (m, 2H), 2.95 (d, 3H), 3.16 (s, 3H), 3.29 (m, 2H), 7.40 (t, 1H), 7.82 (m, 1H), 7.70 (d, 2H), 7.98 (d, 2H), 8.40 (s, 1H), 10.18 (s, 1H) | 377 | Meth 107 |
| 31 | 5-Cyano-2-{4-[N-(3-methoxypropyl)sulphamoyl]anilino}-4-(2-propynylamino)pyrimidine | 1.59 (m, 2H), 2.78 (m, 2H), 3.17 (s, 3H), 3.18 (t, 1H), 3.28 (m, 2H), 4.15 (m, 2H), 7.40 (t, 1H), 8.02 (d, 2H), 8.32 (t, 1H), 8.48 (s, 1H), 8.70 (d, 2H), 10.31 (s, 1H) | 401 | Meth 108 |
| 32 | 5-Cyano-4-cyanomethylamino-2-{4-[N-(3-methoxypropyl)sulphamoyl]anilino} pyrimidine | 1.54 (m, 2H), 2.72 (m, 2H), 3.12 (s, 3H), 3.22 (m, 2H), 4.36 (d, 2H), 7.39 (t, 1H), 7.68 (d, 2H), 7.92 (t, 2H), 8.42 (t, 1H), 8.51 (s, 1H), 10.39 (s, 1H) | 402 | Meth 100 |
| 33 | 5-Cyano-2-{4-[N-(3-methoxypropyl)sulphamoyl]anilino}-4-[N-(methyl)-2,2,2-trifluoroethylamino] pyrimidine | 1.58 (m, 2H), 2.76 (m, 2H), 3.18 (s, 3H), 3.26 (m, 2H), 3.47 (s, 3H), 4.70 (m, 2H), 7.42 (t, 1H), 7.72 (d, 2H), 7.84 (t, 2H), 8.59 (s, 1H), 10.35 (s, 1H) | 459 | Meth 109 |
| 34 | 5-Cyano-4-(2-methoxyethylamino)-2-{4-[N-(3-methoxypropyl)sulphamoyl]anilino} pyrimidine | 1.57 (m, 2H), 2.74 (m, 2H), 3.14 (s, 3H), 3.24 (s & m, 3H & 2H), 3.52 (m, 2H), 3.58 (m, 2H), 7.38 (brt, 1H), 7.68 (d, 2H), 7.84 (brt, 1H), 7.91 (d, 2H), 8.40 (s, 1H), 10.18 (s, 1H) | 421 | Meth 110 |

Examples 35–39

Following the procedure of Example 12 starting from 4-n-butylamino-2-chloro-5-cyanopyrimidine (Method 60) and the appropriate aniline starting material the following compounds were prepared.

| Ex | Compound Name | NMR | m/z | SM |
|----|---------------|-----|-----|-----|
| 35 | 5-Cyano-4-n-butylamino-2-{4-[N-(2-methoxyethyl) sulphamoyl]anilino} pyrimidine | 0.90 (t, 3H), 1.30 (m, 2H), 1.55 (m, 2H), 2.85 (m, 2H), 3.13 (s, 3H), 3.30 (t, 2H), 3.40 (m, 2H), 5.00 (brs, 1H), 7.50 (brs, 1H), 7.70 (d, 2H), 7.9 (d, 3H), 8.40 (s, 1H) | 404 | Meth 5 |
| 36 | 5-Cyano-4-n-butylamino-2-{4-[N-(n-pentyl) sulphamoyl]anilino} pyrimidine | 0.80 (t, 3H), 0.90 (t, 3H), 1.20 (m, 4H), 1.30 (m, 4H), 1.55 (m, 2H), 2.70 (t, 2H), 3.40 (m, 2H), 7.40 (brs, 1H), 7.70 (d, 2H), 7.90 (d, 2H), 8.10 (brs, 1H), 8.40 (s, 1H) | 416 | Meth 8 |
| 37 | 5-Cyano-4-n-butylamino-2-{4-[N-(3-methoxypropyl) sulphamoyl]anilino} pyrimidine | 0.90 (t, 3H), 1.30 (m, 2H), 1.55 (m, 4H), 2.75 (t, 2H), 3.10 (s, 3H), 3.25 (t, 2H), 3.40 (m, 2H), 7.40 (brs, 1H), 7.65 (d, 2H), 7.90 (d, 2H), 8.10 (brs, 1H), 8.40 (s, 1H) | 418 | Meth 4 |
| 38 | 5-Cyano-4-n-butylamino-2-(4-mesylanilino)pyrimidine | 0.90 (t, 3H), 1.35 (m, 2H), 1.60 (m, 2H), 3.15 (s, 3H), 3.40 (m, 2H), 7.80 (d, 2H), 7.95 (d, 2H), 8.15 (brs, 1H), 8.45 (s, 1H) | 345 | Com Av |

Example 39–40

Following the procedure of Example 12 starting from 2-chloro-5-cyano-4-(2,2,2-trifluoroethylamino)pyrimidine (Method 95) and the appropriate aniline starting material the following compounds were prepared.

| Ex | Compound Name | NMR | m/z | SM |
|---|---|---|---|---|
| 39 | 5-Cyano-4-(2,2,2-trifluoroethylamino)-2-{4-[N-(3-methoxypropyl)sulphamoyl]anilino}pyrimidine | 1.55 (m, 2H), 2.75 (q, 2H), 3.10 (s, 3H), 3.30 (t, 2H), 4.22 (m, 2H), 7.40 (t, 1H), 7.65 (d, 2H), 7.90 (d, 2H), 8.40 (t, 1H), 8.50 (s, 1H) | m/z: 444 | Meth 4 |
| 40 | 5-Cyano-4-(2,2,2-trifluoroethylamino)-2-{4-[N-(2-methoxyethyl)sulphamoyl]anilino}pyrimidine | 2.90 (q, 2H), 3.15 (s, 3H), 3.30 (t, 2H), 4.25 (m, 2H), 7.50 (t, 1H), 7.70 (d, 2H), 7.85 (d, 2H), 8.40 (t, 1H), 8.50 (s, 1H) | 430 | Meth 5 |

Examples 41–42

Following the procedure of Example 12 starting from 2-chloro-5-cyano-4-ethylaminopyrimidine (Method 56) and the appropriate aniline starting material the following compounds were prepared.

| Ex | Compound Name | NMR | m/z |
|---|---|---|---|
| 41 | 5-Cyano-4-ethylamino-2-(4-mesylanilino)pyrimidine | 1.20 (t, 3H), 3.15 (s, 3H), 3.45 (m, 2H), 7.80 (d, 2H), 8.00 (m, 3H), 8.40 (s, 1H) | 317 |
| 42[1] | 5-Cyano-4-ethylamino-2-[4-(N-allylsulphamoyl)anilino]pyrimidine | 1.18 (t, 3H), 3.37 (d, 2H), 3.50 (m, 2H), (d, 1H), 5.10 (d, 1H), 5.63 (m, 1H), (brs, 1H), 7.70 (d, 2H), 7.90 (d, 2H), 8.10 (brs, 1H), 8.42 (s, 1H), 10.65 (brs, 1H) | 359 |

[1] Aniline - Method 6

Example 43

5-Cyano-4-butylamino-2-{4-[N-(tetrahydrofur-2-ylmethyl)sulphamoyl]anilino}pyrimidine 4-Butylamino-5-N-t-butylcarbamoyl-2-{4-[N-(tetrahydrofur-2-ylmethyl)sulphamoyl]anilino}pyrimidine (Method 67; 200 mg, 0.40 mmol) in thionyl chloride (1 ml) was heated at 90° C. for 12 hours. The mixture was allowed to cool and then was evaporated onto silica. The residue was purified by chromatography eluting with DCM/methanol (100:0) increasing in polarity to (97:3). The product was recrystallized from methanol to give the title compound (33 mg). NMR: 0.90 (t, 3H), 1.34 (m, 2H), 1.41–1.63 (m, 3H), 1.66–1.88 (m, 3H), 2.73 (t, 2H), 3.40 (m, 2H), 3.53 (m, 1H), 3.64 (m, 1H), 3.77 (m, 1H), 7.51 (t, 1H), 7.67 (d, 2H), 7.88 (brs, 1H), 7.91 (d, 2H), 8.37 (s, 1H), 10.13 (brs, 1H); m/z: 431.

Example 44–54

Following the procedure of Example 43 using the appropriate 4-substituted amidopyrimidine starting material the following compounds were prepared.

| Ex | Compound Name | NMR | m/z | SM |
|---|---|---|---|---|
| 44[1] | 5-Cyano-4-(2,2,2-trifluoro-ethylamino)-2-{4-[N-(tetrahydrofur-2-ylmethyl)sulphamoyl]anilino}pyrimidine | 1.50 (m, 1H), 1.68–1.89 (m, 3H), 2.74 (t, 2H), 3.54 (m, 1H), 3.63 (m, 1H), 3.76 (m, 1H), 4.22 (m, 2H), 7.54 (t, 1H), 7.69 (d, 2H), 7.86 (d, 2H), 8.39 (t, 1H), 8.51 (s, 1H), 10.31 (brs, 1H) | 457 | Meth 68 |
| 45[1,2] | 5-Cyano-4-[bis-(2-cyanoethyl)amino]-2-{4-[N-(tetrahydrofur-2-ylmethyl)sulphamoyl]anilino}pyrimidine | 1.50 (m, 1H), 1.65–1.88 (m, 3H), 2.74 (t, 2H), 2.95 (t, 4H), 3.54 (m, 1H), 3.65 (m, 1H), 3.77 (m, 1H), 3.98–4.09 (m, 4H), 7.52 (t, 1H), 7.72 (d, 2H), 7.82 (d, 2H), 8.54 (s, 1H), 10.31 (brs, 1H) | 481 | Meth 69 |
| 46[3] | 5-Cyano-4-(cyclopropylamino)-2-{4-[N-(tetrahydrofur-2-ylmethyl)sulphamoyl]anilino}pyrimidine | 0.68 (m, 2H), 0.80 (m, 2H), 1.50 (m, 1H), 1.69–1.88 (m, 3H), 2.73 (t, 2H), 2.87 (m, 1H), 3.54 (m, 1H), 3.65 (m, 1H), 3.76 (m, 1H), 7.47 (t, 1H), 7.69 (d, 2H), 8.02 (s, 1H), 8.06 (d, 2H), 8.38 (s, 1H), 10.20 (brs, 1H). | 415 | Meth 70 |
| 47[3] | 5-Cyano-4-(cyclopropylmethylamino)-2-{4-[N-(tetrahydrofur-2-ylmethyl)sulphamoyl]anilino}pyrimidine | 0.02 (m, 2H), 0.19 (m, 2H), 0.91 (m, 1H), 1.26 (m, 1H), 1.44–1.64 (m, 3H), 2.50 (t, 2H), 3.05 (t, 2H), 3.31 (m, 1H), 3.38–3.58 (m, 2H), 7.29 (t, 1H), 7.44 (d, 2H), 7.66 (d, 2H), 7.78 (t, 1H), 8.17 (s, 1H), 9.93 (s, 1H). | 429 | Meth 71 |
| 48[3] | 5-Cyano-4-(cyclohexylamino)-2-{4-[N-(tetrahydrofur-2-ylmethyl)sulphamoyl]anilino}pyrimidine | 1.08–1.56 (m, 6H), 1.60–1.93 (m, 8H), 2.72 (brs, 2H), 3.54 (m, 1H), 3.65 (m, 1H), 3.77 (m, 1H), 3.95 (brs, 1H), 7.54 (brs, 1H), 7.64 (brs, 1H), 7.70 (d, 2H), 7.90 (d, 2H), 8.38 (s, 1H), 10.20 (brs, 1H). | 457 | Meth 72 |
| 49[3] | 5-Cyano-4-(tetrahydrofur-2-ylmethylamino)-2-{4-[N-(tetrahydrofur-2-ylmethyl)sulphamoyl]anilino}pyrimidine | 1.50 (m, 1H), 1.63 (m, 1H), 1.70–1.96 (m, 6H), 2.73 (t, 2H), 3.36–3.60 (m, 3H), 3.64 (m, 2H), 3.77 (m, 2H), 4.09 (m, 1H), 7.51 (t, 1H), 7.67 (d, 2H), 7.84 (t, 1H), 7.91 (d, 2H), 8.39 (s, 1H), 10.15 (brs, 1H) | 459 | Meth 73 |
| 50[4] | 5-Cyano-4-(pyrid-3-ylmethylamino)-2-{4-[N-(tetrahydrofur-2-ylmethyl)sulphamoyl]anilino}pyrimidine | 1.50 (m, 1H), 1.65–1.87 (m, 3H), 2.70 (m, 2H), 3.46–3.82 (m, 3H), 4.63 (d, 2H), 7.34 (m, 1H), 7.50 (m, 1H), 7.6 (m, 2H), 7.72 (m, 3H), 8.4 (m, 2H), 8.50 (m, 1H), 8.58 (s, 1H), 10.14 (brs, 1H) | 466 | Meth 74 |
| 51[4] | 5-Cyano-4-(piperidino)-2-{4-[N-(tetrahydrofur-2-ylmethyl)sulphamoyl]anilino}pyrimidine | 1.42 (m, 10H), 2.73 (t, 2H), 3.54 (m, 1H), 3.65 (m, 1H), 3.72–3.90 (m, 9H), 7.50 (t, 1H), 7.69 (d, 3H), 7.83 (d, 2H), 8.44 (s, 1H), 10.15 (brs, 1H) | 443 | Meth 75 |
| 52[4] | 5-Cyano-4-[N-(ethyl)-cyclohexylamino]-2-{4-[N-(tetrahydrofur-2-ylmethyl)sulphamoyl]anilino}pyrimidine | 1.20 (t, 3H), 1.25–1.86 (m, 14H), 2.73 (t, 2H), 3.48–3.80 (m, 5H), 4.58 (m, 1H), 7.54 (t, 1H), 7.68 (d, 2H), 7.84 (d, 2H), 8.40 (s, 1H), 10.13 (brs, 1H) | 485 | Meth 76 |
| 53[5] | 5-Cyano-4-(n-butoxycarbonyl methylamino)-2-{4-[N-(tetrahydrofur-2-ylmethyl)sulphamoyl]anilino}pyrimidine | 0.78 (t, 3H), 1.20 (m, 2H), 1.38 (m, 2H), 1.64–1.92 (m, 3H), 3.73 (m, 2H), 3.48–3.80 (m, 4H), 4.00 (t, 2H), 4.12 (d, 2H), 7.52 (m, 1H), 7.65 (d, 2H), 7.80 (d, 2H), 8.23 (m, 1H), 8.46 (s, 1H), 10.22 (brs, 1H) | 489 | Meth 77 |
| 54[5] | 5-Cyano-4-(2-methoxycarbonyl ethylamino)-2-{4-[N-(tetrahydrofur-2-ylmethyl)sulphamoyl]anilino}pyrimidine | 1.50 (m, 1H), 1.67–1.9 (m, 3H), 2.70 (m, 4H), 3.48–3.80 (m, 6H), 4.02 (m, 2H), 7.54 (m, 1H), 7.66 (d, 2H), 7.89 (d, 2H), 8.50 (s, 1H), 8.95 (m, 1H), 10.18 (brs, 1H) | 461 | Meth 78 |

[1] Reaction mixture was heated at 90° C. for 3 hours.
[2] Chromatography eluent was isohexane/ethyl acetate (100:0) increasing in polarity to (0:100).
[3] Reaction mixture was heated at 90° C. for 6 hours.
[4] mixture was heated at 95° C. for 3 hours.
[5] Reaction mixture was heated at 95° C. for 4 hours.

Examples 55-56

Following the procedure of Example 1, 2-chloro-5-cyano-4-morpholinopyrimidine (Method 55) was treated with the appropriate aniline to give the following compounds.

| Ex | Compound Name | NMR | m/z | SM |
|---|---|---|---|---|
| 55 | 5-Cyano-4-morpholino-2-(4-sulphamoylanilino)pyrimidine | 3.70(t, 4H), 3.86(m, 4H), 7.20(s, 2H), 7.73(d, 2H), 7.80(d, 2H), 8.50(s, 1H), 10.22(s, 1H) | 359 (MH)⁻ | Com Av |
| 56 | 5-Cyano-4-morpholino-2-{4-[N-(3-hydroxy-2,2-dimethylpropyl)sulphamoyl]anilino}pyrimidine | 0.73(s, 6H), 2.50(d, 2H), 3.07(s, 1H), 3.70(t, 4H), 3.87(t, 4H), 7.22 (t, 1H), 7.70(d, 2H), 7.83(d, 2H), 8.50(s, 1H), 10.25(s, 1H) | 447 | Meth 3 |

Example 57

4-[4-(2-Hydroxyethyl)piperazin-1-yl]-5-cyano-2-{4-[N-(3-methoxypropyl)sulphamoyl]anilino}pyrimidine 4-[4-(2-Acetoxyethylpiperazin-1-yl)]-5-cyano-2-{4-[N-(3-methoxypropyl)sulphamoyl]anilino}pyrimidine (Method 119; 290 mg) was dissolved in methanol (3 ml), 35% ammonia (1.5 ml) was added and the reaction was stirred at room temperature for 2 hours. The volatiles were evaporated and the residue purified by chromatography on silica gel, eluting with DCM/methanol (98:2) increasing in polarity to (95:5). The resulting solid was triturated with ethyl acetate/diethyl ether and collected by filtration to yield the title compound (19 mg) NMR: 1.55 (m, 2H), 2.45 (2H), 2.55 (brt, 4H), 2.75 (q, 2H), 3.14 (s, 3H), 3.26 (2H), 3.50 (q, 2H), 3.88 (brt, 4H), 4.42 (t, 1H), 7.35 (t, 1H), 7.68 (d, 2H), 7.84 (d, 2H), 8.48 (s, 1H), 10.21 (s, 1H); m/z: 476.

Example 58

5-Cyano-4-cyclopropylamino-2-{4-[N-(2-methoxyethyl)sulphamoyl]anilino}pyrimidine 2-Chloro-5-cyano-4-cyclopropylaminopyrimidine (Method 96; 295 mg, 1.28 mmol) was dissolved in hot 2-butanol (3 ml). A hot solution of 4-[N-(2-methoxyethyl)sulphamoyl]aniline (Method 5; 207 mg, 0.90 mmol) in 2-butanol (3 ml) was added and the reaction was stirred and heated at 90° C. for 1 hour. The reaction mixture was cooled and the volatiles evaporated to give a solid. The solid residue was triturated with hot ethyl acetate, cooled, and the resultant solid collected by filtration to give the title compound (270 mg, 77%). NMR: 0.68 (m, 2H), 0.80 (m, 2H), 2.88 (m, 3H), 3.14 (s, 3H), 3.28 (m, 2H), 7.48 (brs, 1H), 7.70 (d, 2H), 8.05 (d, 2H), 8.12 (brs, 1H) 8.41 (s, 1H), 10.31 (s, 1H); m/z: 389.

Examples 59-72

The following examples were prepared using the procedure of Example 58 starting from 2-chloro-5-cyano-4-cyclopropylaminopyrimidine (Method 96) and the appropriate aniline.

| Ex | Compound Name | NMR | m/z | SM |
|---|---|---|---|---|
| 59 | 5-Cyano-4-cyclopropylamino-2-{4-[N-(3-methoxypropyl)sulphamoyl]anilino}pyrimidine | 0.68(m, 2H), 0.80(m, 2H), 1.57(m, 2H), 2.74(m, 2H), 2.88(m, 1H), 3.12(s, 3H), 3.25(m, 2H), 7.48(brs, 1H), 7.70(d, 2H), 8.05(d, 2H), 8.12(brs, 1H) 8.41(s, 1H), 10.31(s, 1H) | 403 | Meth 4 |
| 60 | 5-Cyano-4-cyclopropylamino-2-[4-(ethylsulphonyl)anilino]pyrimidine | 0.68(m, 2H), 0.83(m, 2H), 1.08(t, 3H), 2.88(m, 1H), 3.20(q, 2H), 7.78(d, 2H), 8.12(d and s, 3H), 8.41(s, 1H), 10.37(brs, 1H) | 344 | Ref[1] |
| 61 | 5-Cyano-4-cyclopropylamino-2-{4-[(2-ethoxyethyl)sulphonyl]anilino}pyrimidine | 0.68(m, 2H), 0.82(m, 2H), 0.90(t, 3H), 2.86(m, 1H), 3.28(q, 2H), ), 3.46(m, 2H), 3.60(m, 2H), 7.78(d, 2H), 8.10(d, 2H), 8.15(brs, 1H), 8.41(s, 1H), 10.37(brs, 1H) | 388 | Ref[2] |
| 62 | 5-Cyano-4-cyclopropylamino-2-[4-(propylsulphonyl)anilino]pyrimidine | 0.68(m, 2H), 0.82(m, 2H), 0.88(t, 3H), 1.52(m, 2H), 2.86(m, 1H), 3.18(m, 2H), 7.79(d, 2H), 8.13(s and d, 3H), 8.42(s, 1H), 10.39(brs, 1H) | 358 | Ref[1] |
| 63 | 5-Cyano-4-cyclopropylamino-2-(4-mesylanilino)pyrimidine | 0.68(m, 2H), 0.82(m, 2H), 0.88(t, 3H), 2.86(m, 1H), 3.12(s, 3H), 7.82(d, 2H), 8.10(d, 2H), 8.17(brs, 1H), 8.42(s, 1H), 10.40(brs, 1H) | 330 | Com Av |
| 64 | 5-Cyano-4-cyclopropyl-amino-2-{4-[2-(diethylamino)ethylsulphonyl]anilino)pyrimidine | 0.68(m, 2H), 0.82(m, 8H), 2.33(m, 4H), 2.68(m, 2H), 2.85(m, 1H), 3.30(m, 2H), 7.81(d, 2H), 8.10(s, 1H), 8.14(d, 2H), 8.41(s, 1H), 10.31(s, 1H) | 415 | Com Av |
| 65 | 5-Cyano-4-cyclopropylamino-2-{4-[N-(2-diethylaminoethyl)sulphamoyl]anilino}pyrimidine | 0.71(m, 2H), 0.82(m, 2H), 0.87(t, 6H), 2.38(m, 6H), 2.78(m, 2H), 2.88(m, 1H), 7.21(brs, 1H), 7.71(d, 2H), 8.08(d and s, 3H), 8.41(s, 1H), 10.24(s, 1H) | 430 | Meth 17 |
| 66 | 5-Cyano-4-cyclopropylamino-2-{4-[N-(2-diethylaminoethyl)-N-(methyl)sulphamoyl]anilino}pyrimidine | 0.68(m, 2H), 0.85(m, 2H), 0.93(t, 6H), 2.45(m, 6H), 2.70(s, 3H), 2.88(m, 1H), 3.00(m, 2H), 7.71(d, 2H), 8.09(brs, 1H), 8.14(d, 2H), 8.43(s, 1H), 10.28(s, 1H) | 444 | Meth 18 |
| 67 | 5-Cyano-4-cyclopropylamino-2-{4-[N-(2-methoxyethyl)-N-(methyl)sulphamoyl]anilino}pyrimidine | 0.68(m, 2H), 0.82(m, 2H), 2.68(s, 3H), 2.88(m, 1H), 3.08(t, 2H), 3.20(s, 3H), 3.42(t, 2H), 7.68(d, 2H), 8.09(d, 3H), 8.40(s, 1H), 10.38(brs, 1H) | 403 | Meth 16 |
| 68 | 5-Cyano-4-cyclopropylamino-2-(4-{N-[2-(piperidino)ethyl]sulphamoyl}anilino)pyrimidine | 0.68(m, 2H), 0.78(m, 2H), 1.30(m, 2H), 1.40(m, 4H), 2.18(m, 4H), 2.23(t, 2H), 2.80(t, 2H), 2.85(m, 1H), 7.19(brs, 1H), 7.70(d, 2H), 8.02(s, 1H), 8.08(d, 2H), 8.38(s, 1H), 10.19(brs, 1H) | 442 | Meth 7 |
| 69 | 5-Cyano-4-cyclopropylamino-2-{4-[3-(isopropylamino)propylsulphonyl]anilino}pyrimidine | 0.69(m, 2H), 0.82(m, 2H), 1.18(d, 6H), 1.90(brquin, 2H), 2.90(m, 3H), 3.19(m, 1H), 3.40(m, 2H), 7.80(d, 2H), 8.12(brs, 1H), 8.19(d, 2H), 8.25–8.90(brs, 1H), 8.41(s, 1H), 10.35(s, 1H) | 415 | Meth 30 |
| 70 | 5-Cyano-4-cyclopropylamino-2-{4-[4-(isopropylamino)butylsulphonyl]anilino}pyrimidine | 0.68(m, 2H), 0.82(m, 2H), 1.20(d, 6H), 1.60(m, 2H), 1.68(m, 2H), 2.83(m, 3H), 3.17(m, 1H), 3.28(m, 2H), 7.80(d, 2H), 8.10(s, 1H), 8.16(d, 2H), 8.41(s, 1H), 8.68(brs, 2H), 10.34(s, 1H) | 429 | Meth 29 |
| 71 | 5-Cyano-4-cyclopropylamino-2-{4-[N-(3-piperidinopropyl)sulphamoyl]anilino}pyrimidine hydrochloride | 0.68(m, 2H), 0.81(m, 2H), 1.21(t, 1H), 1.35(m, 1H), 1.68(m, 1H), 1.72(m, 4H), 1.80(m, 2H), 2.78(m, 4H), 2.86(m, 1H), 2.95(m, 2H), 3.06(m, 1H), 7.58(t, 1H), 7.71(d, 2H), 8.08(d, 3H), 8.40(s, 1H), 9.92(brs, 1H), 10.19(brs, 1H) | 456 | Meth 19 |
| 72 | 5-Cyano-4-cyclopropylamino-2-{4-[N-(methyl)-N-(3-piperidinopropyl)sulphamoyl]anilino}pyrimidine hydrochloride | 0.68(m, 2H), 0.82(m, 2H), 1.37(brm, 1H), 1.73(m, 4H), 1.92(brm, 5H), 2.18(m, 4H), 2.64(s, 3H), 2.83(m, 3H), 2.98(m, 4H), 3.37(brt, 2H), 7.69(d, 2H), 8.08(s, 1H), 8.13(d, 2H), 8.40(s, 1H), 9.96(brs, 1H), 10.28(brs, 1H) | 470 | Meth 20 |

[1] Helv. Chim. Acta, 66(4) 1046–52(1983)
[2] Kogyo Kagaku Zasshi, 62 825–8(1959)

Example 73

5-Cyano-4-ethylamino-2-{4-[N-(3-methoxypropyl) sulphamoyl]anilino}pyrimidine 5-Cyano-4-ethylamino-2-[(4-fluorosulphonyl)anilino]pyrimidine (Method 111; 50 mg, 0.16 mmol), 3-methoxypropylamine (28 mg, 0.31 mmol) and polymer supported 4-(dimethylamino)pyridine (supplied by Argonout Technologies Inc; 1.45 mmol/l) (218 mg, 0.31 mmol) in NMP (1 ml) were heated at 100° C. for 18 hours. Volatiles were removed by evaporation and the residue was triturated with ether. The resultant solid was purified by reverse phase chromatography (Waters xterra 19×50 mm column) (0.1% formic acid in a gradient of 0–95% acetonitrile in water) to give the title compound (16 mg, 26%). NMR: 1.18 (t, 3H), 1.57 (m, 2H), 2.75 (m, 2H), 3.13 (s, 3H), 3.25 (m, 2H), 3.43 (m, 2H), 7.35 (m, 1H), 7.65 (d, 2H), 7.82 (m, 1H), 7.94 (d, 2H), 8.39 (s, 1H), 10.13 (s, 1H), m/z: 391.

Examples 74–100

Following the procedure of Example 73, 5-Cyano-4-ethylamino-2-[(4-fluorosulphonyl)anilino]pyrimidine (Method 111) was treated with the appropriate amine to give the following compounds.

| Ex | Compound Name | m/z |
|---|---|---|
| 74 | 5-Cyano-4-ethylamino-2-{4-[N-(3-ethoxypropyl)sulphamoyl]anilino}-pyrimidine | 405 |
| 75 | 5-Cyano-4-ethylamino-2-{4-[N-(3-imidazolylpropyl)sulphamoyl]anilino}pyrimidine | 427 |
| 76 | 5-Cyano-4-ethylamino-2-(4-{N-[3-(2-dimethylaminoethoxy)propyl]sulphamoyl}anilino)pyrimidine | 448 |
| 77 | 5-Cyano-4-ethylamino-2-{4-[N-(3-morpholinopropyl)sulphamoyl]anilino}pyrimidine | 446 |
| 78 | 5-Cyano-4-ethylamino-2-{4-[N-(2-pyrrolidinylethyl)sulphamoyl]anilino}pyrimidine | 416 |
| 79 | 5-Cyano-4-ethylamino-2-(4-{N-[2-(1-ethylpyrrolidin-2-yl)ethyl]sulphamoyl}anilino)pyrimidine | 430 |
| 80 | 5-Cyano-4-ethylamino-2-{4-[N-(2-pyridin-2-ylethyl)sulphamoyl]anilino}pyrimidine | 424 |
| 81 | 5-Cyano-4-ethylamino-2-{4-[N-(pyridin-3-ylmethyl)sulphamoyl]anilino}pyrimidine | 410 |
| 82 | 5-Cyano-4-ethylamino-2-{4-[N-(2-piperidinoethyl)sulphamoyl]anilino}pyrimidine | 430 |
| 83 | 5-Cyano-4-ethylamino-2-{4-[N-(2-diethylaminoethyl)sulphamoyl]anilino}pyrimidine | 418 |
| 84 | 5-Cyano-4-ethylamino-2-{4-[N-(2-pyridin-4-ylethyl)sulphamoyl]anilino}pyrimidine | 424 |
| 85 | 5-Cyano-4-ethylamino-2-{4-[N-(pyridin-2-ylmethyl)sulphamoyl]anilino}pyrimidine | 410 |
| 86 | 5-Cyano-4-ethylamino-2-{4-[N-(2-acetamidoethyl)sulphamoyl]anilino}pyrimidine | 404 |
| 87 | 5-Cyano-4-ethylamino-2-{4-[N-(2-isopropylaminoethyl)sulphamoyl]anilino}pyrimidine | 404 |
| 88 | 5-Cyano-4-ethylamino-2-{4-[N-(2-dimethylaminoethyl)sulphamoyl]anilino}pyrimidine | 390 |
| 89 | 5-Cyano-4-ethylamino-2-{4-[N-(2-morpholinoethyl)sulphamoyl]anilino}pyrimidine | 432 |
| 90 | 5-Cyano-4-ethylamino-2-{4-[N-(dioxan-2-ylmethyl)sulphamoyl]anilino}pyrimidine | 419 |
| 91 | 5-Cyano-4-ethylamino-2-{4-[N-(tetrahydrofur-2-ylmethyl)sulphamoyl]anilino}pyrimidine | 403 |
| 92 | 5-Cyano-4-ethylamino-2-{4-[N-(2-hydroxypropyl)sulphamoyl]anilino}pyrimidine | 377 |
| 93 | 5-Cyano-4-ethylamino-2-{4-[N-(2-propynyl)sulphamoyl]anilino}pyrimidine | 418 |
| 94 | 5-Cyano-4-ethylamino-2-{4-[N-(3-hydroxy-2,2-dimethylpropyl)sulphamoyl]anilino}pyrimidine | 405 |
| 95 | 5-Cyano-4-ethylamino-2-[4-(N-methylsulphamoyl)anilino]pyrimidine | 333 |
| 96 | 5-Cyano-4-ethylamino-2-(4-{N-[2-(2-hydroxyethyl)ethoxy]sulphamoyl}anilino)pyrimidine | 407 |
| 97 | 5-Cyano-4-ethylamino-2-{4-[N-(2-hydroxyethyl)sulphamoyl]anilino}pyrimidine | 363 |
| 98 | 5-Cyano-4-ethylamino-2-{4-[N-(5-hydroxypentyl)sulphamoyl]anilino}pyrimidine | 405 |
| 99 | 5-Cyano-4-ethylamino-2-{4-[N-(2-hydroxybutyl)sulphamoyl]anilino}pyrimidine | 391 |
| 100 | 5-Cyano-4-ethylamino-2-{4-[N-(2-cyanoethyl)sulphamoyl]anilino}pyrimidine | 377 |

Example 101

5-Cyano-4-n-butylamino-2-{4-[N-(ethylthioethyl)sulphamoyl]anilino}pyrimidine

5-Cyano-4-butylamino-2-[(4-fluorosulphonyl)anilino]pyrimidine (Method 112; 200 mg, 0.57 mmol), 2-(ethylthio)ethylamine (480 mg, 4.56 mmol), triethylamine (58 mg, 0.57 mmol) and 4-(dimethylamino)pyridine (7 mg, 0.06 mmol) in 1-butanol (6 ml) was heated at 95° C. for 24 hours. The mixture was allowed to cool and the solvent was removed by evaporation. The resulting solid was recrystallized from ethanol to give the title compound (130 mg). NMR: 0.90 (t, 3H), 1.10 (t, 3H), 1.35 (m, 2H), 1.59 (m, 2H), 2.40–2.60 (m, 4H), 2.90 (t, 2H), 3.40 (q, 2H), 7.70 (d, 2H), 7.80–8.88 (m, 3H), 8.40 (s, 1H); m/z: 434.

Example 102–108

Starting from 5-cyano-4-butylamino-2-[(4-fluorosulphonyl)anilino]pyrimidine (Method 112) and the appropriate amines the following compounds were prepared using the procedure in Example 101.

| Ex | Compound Name | NMR | m/z |
|---|---|---|---|
| 102 | 5-Cyano-4-n-butylamino-2-{4-[N-(2-morpholinoethyl)sulphamoyl]anilino}pyrimidine | 0.90(t, 3H), 1.35(m, 2H), 1.59(m, 2H), 2.30 (m, 6H), 2.81(t, 2H), 3.39–3.60(m, 6H), 7.75 (d, 2H), 7.90(m, 3H), 8.39(s, 1H) | 459 |
| 103 | 5-Cyano-4-n-butylamino-2-{4-[N-(3-imidazol-1-ylpropyl)sulphamoyl]anilino}pyrimidine | 0.95(t, 3H), 1.35(m, 2H), 1.59(m, 2H), 1.80 (m, 2H), 2.65(t, 2H), 3.40(q, 2H), 3.90(t, 2H), 6.81(s, 1H), 7.05(s, 1H), 7.50(s, 1H), 7.65(d, 2H), 7.90(m, 3H), 8.39(s, 1H) | 454 |
| 104 | 5-Cyano-4-n-butylamino-2-{4-[N-(2-piperidinoethyl)sulphamoyl]anilino}pyrimidine | 0.95(t, 3H), 1.20–1.50(m, 8H), 1.55(m, 2H), 2.20(brm, 6H), 2.80(t, 2H), 3.40(q, 2H), 7.25 (brs, 1H), 7.65(d, 2H), 7.90(m, 3H), 8.40(s, 1H) | 457 |
| 105 | 5-Cyano-4-n-butylamino-2-{4-[N-(2-pyrid-2-ylethyl)sulphamoyl]anilino}pyrimidine | 0.95(t, 3H), 1.30(m, 2H), 1.60(m, 2H), 2.80 (t, 3H), 3.10(m, 2H), 3.40(q, 2H), 7.20(m, 2H), 7.50(brs, 1H), 7.65(m, 3H), 7.90(m, 3H), 8.35(s, 1H), 8.40(d, 1H) | 451 |
| 106 | 5-Cyano-4-n-butylamino-2-{4-[N-(2-pyrrolidin-1-ylethyl)sulphamoyl]anilino}pyrimidine | 0.90(t, 3H), 1.35(m, 2H), 1.60(m, 6H), 2.20–2.40 (m, 6H), 2.80(t, 2H), 3.40(q, 2H), 7.30 (brs, 1H), 7.70(d, 2H), 7.9(m, 3H), 8.38(s, 1H) | 443 |
| 107 | 5-Cyano-4-n-butylamino-2-{4-[N-(3-amino-2-hydroxypropyl)sulphamoyl]anilino}pyrimidine | 0.90(t, 3H), 1.40(m, 2H), 1.60(m, 2H), 2.40 (m, 1H), 2.60(m, 1H), 2.70(m, 1H), 2.80(m, 1H), 3.45(m, 2H), 7.70(d, 1H), 7.90(m, 3H), 8.40(s, 1H), 10.15(brs, 1H) | 419 |
| 108 | 5-Cyano-4-n-butylamino-2-{4-[N-(2-isopropylaminoethyl)sulphamoyl]anilino}pyrimidine | 0.90(m, 9H), 1.40(m, 2H), 1.60(m, 2H), 2.60 (m, 1H), 2.80(t, 2H), 3.45(q, 2H), 7.70(d, 2H), 7.9(m, 3H), 8.40(s, 1H), 10.20(s, 1H) | 431 |

Example 109

5-Cyano-4-(2,2,2-trifluoroethylamino)-2-{4-[N-(2-imidazo-4-1ylethyl)sulphamoyl]anilino}pyrimidine 5-Cyano-4-(2,2,2-trifluoroethylamino)-2-[(4-fluorosulphonyl)anilino]pyrimidine (Method 113; 200 mg, 0.53 mmol), histamine (466 mg, 4.24 mmol), triethylamine (54 mg, 0.53 mmol) and 4-(dimethylamino)pyridine (7 mg, 0.05 mmol) in 2-butanol (6 ml) was heated at 95° C. for 48 hours. The mixture was allowed to cool and the solvent was removed by evaporation. The resulting solid was recrystallized from ethanol to give the title compound (80 mg). NMR: 2.70 (m, 2H), 3.10 (t, 2H), 4.30 (m, 2H), 6.70 (s, 1H), 7.40 (s, 1H), 7.70 (d, 2H), 7.90 (d, 2H), 8.50 (s, 1H); m/z: 466

Example 110–114

Starting from 5-cyano-4-(2,2,2-trifluoroethylamino)-2-[(4-fluorosulphonyl)anilino]pyrimidine (Method 113) and the appropriate amines the following compounds were prepared using the procedure of Example 109.

| Ex | Compound Name | NMR | m/z |
|---|---|---|---|
| 110 | 5-Cyano-4-(2,2,2-trifluoroethylamino)-2-{4-[N-(2-mesylethyl)sulphamoyl]anilino}pyrimidine | 2.99(s, 3H), 3.00–3.40(m, 7H), 4.25 (m, 2H), 7.70(d, 2H), 7.90(d, 2H), 8.40 (brs, 1H), 8.50(s, 1H) | 478 |
| 111 | 5-Cyano-4-(2,2,2-trifluoroethylamino)-2-(4-{N-[2-(2-hydroxyethoxy)ethyl]sulphamoyl}anilino)pyrimidine | 2.90(q, 2H), 3.40–3.60(m, 6H), 4.25 (m, 2H), 4.55(t, 1H), 7.55(t, 1H), 7.70 (d, 2H), 7.90(d, 2H), 8.40(t, 1H), 8.55 (s, 1H), 10.40(s, 1H) | 460 |
| 112 | 5-Cyano-4-(2,2,2-trifluoroethylamino)-2-{4-[N-(3-hydroxypropyl)sulphamoyl]anilino}pyrimidine | 1.50(m, 2H), 2.80(t, 2H), 3.35(m, 2H), 4.30(q, 2H), 4.45(t, 1H), 7.40(brs, 1H), 7.75(d, 2H), 7.90(d, 2H), 8.40 (brs, 1H), 8.55(s, 1H), 10.40(brs, 1H) | 430 |
| 113 | 5-Cyano-4-(2,2,2-trifluoroethylamino)-2-{4-[N-(2-methyl-1,3,4-triazol-5-yl)sulphamoyl]anilino}pyrimidine | 2.20(brm, 3H), 2.75(brm, 2H), 3.00 (brm, 2H), 4.20(q, 2H), 7.50(brs, 1H), 7.75(d, 2H), 7.90(d, 2H), 8.40(t, 1H), 8.50(s, 1H) | 481 |
| 114 | 5-Cyano-4-(2,2,2-trifluoroethylamino)-2-{4-[N-(2-hydroxyethyl)sulphamoyl]anilino}pyrimidine | 2.80(q, 2H), 3.40(t, 2H), 4.25(m, 2H), 7.40(t, 1H), 7.70(d, 2H), 7.90(d, 2H), 8.40(t, 1H), 8.55(s, 1H), 10.40(brs, 1H) | 416 |

Example 115

5Cyano-4-(2,3-dihydroxypropylamino)-2-{4-[N-(3-methoxypropyl)sulphamoyl]anilino}pyrimidine A suspension of 2-chloro-4-(4-chlorophenoxy)-5-cyanopyrimidine (Method 115; 179 mg, 0.68 mmol) and 4-[N-(3-methoxypropyl)sulphamoyl]aniline (Method 4; 149 mg, 0.61 mmol) in 2-butanol (6 ml) was heated and stirred at 50° C. for 5 hours. 3-Amino-1,2-propanediol (309 mg, 3.4 mmol) was then added and the temperature was raised to 90° C. and the reaction was stirred at this temperature for a further 18 hours. The solvent was removed by evaporation and the resulting solid was recrystallized from ethanol to give the title compound (104 mg, 39%). NMR: 1.55 (m, 2H), 2.75 (m, 2H), 3.15 (s, 3H), 3.25 (m, 2H), 3.40 (m, 3H), 3.60 (m, 1H), 3.75 (m, 1H), 4.70 (t, 1H), 5.85 (m, 1H), 7.35 (t, 1H), 7.55 (brs, 1H), 7.70 (d, 2H), 7.95 (d, 2H), 8.40 (s, 1H), 10.20 (s, 1H); m/z: 436.

Example 116–129

Starting from 2-chloro-4-(4-chlorophenoxy)-5-cyanopyrimidine (Method 115), the appropriate anilino sulphonamide/sulphone (see column SM) and the appropriate amines following the procedure in Example 115 the following compounds were prepared.

| Ex | Compound Name | NMR | m/z | SM |
|---|---|---|---|---|
| 116 | 5-Cyano-4-(3-hydroxypyrrolidin-1-yl)-2-{4-[N-(2-methoxyethyl)sulphamoyl]anilino}pyrimidine | 1.95(brs, 2H), 2.90(q, 2H), 3.15(s, 3H), 3.25(m, 2H), 3.60–3.90(brm, 4H), 4.40(brs, 1H), 5.05(brs, 1H), 7.50(brs, 1H), 7.75(d, 2H), 7.90(d, 2H), 8.40(s, 1H) | 418 | Meth 5 |
| 117 | 5-Cyano-4-[N-methyl-N-(2-propynyl)amino]-2-{4-[N-(3-methoxypropyl)sulphamoyl]anilino}pyrimidine | 1.55(m, 2H), 2.75(m, 2H), 3.15(s, 3H), 3.25(m, 2H), 3.30(s, 1H), 3.70 (s, 3H), 4.50(s, 2H), 7.40(t, 1H), 7.70 (d, 2H), 7.90(d, 2H), 8.50(s, 1H) | 414 | Meth 4 |
| 118 | 5-Cyano-4-(2,2-dimethyldioxolan-4-ylmethylamino)-2-{4-[N-(3-methoxypropyl)sulphamoyl]anilino}pyrimidine | 1.21(s, 3H), 1.35(s, 3H), 1.58(m, 2H), 2.75(m, 2H), 3.10(s, 3H), 3.25 (m, 2H), 3.55(m, 2H), 3.76(m, 1H), 3.95(m, 1H), 4.30(m, 1H), 7.40(t, 1H), 7.65(d, 2H), 7.85(t, 1H), 7.9(d, 2H), 8.40(s, 1H) | 476 | Meth 4 |
| 119 | 5-Cyano-4-(2-imidazol-4-ylethylamino)-2-{4-[N-(3-methoxypropyl)sulphamoyl]anilino}pyrimidine | 1.65(m, 2H), 2.80–3.00(m, 4H), 3.20 (s, 3H), 3.35(t, 2H), 3.75(m, 2H), 6.82(brs, 1H), 7.02(brs, 1H), 7.50(s, 1H), 7.55(brs, 1H), 7.70(d, 2H), 7.95 (d, 2H), 8.35(s, 1H), 9.80(brs, 1H) | 456 | Meth 4 |
| 120 | 5-Cyano-4-[2-(2-hydroxyethoxy)ethylamino]-2-{4-[N-(3-methoxypropyl)sulphamoyl]anilino}pyrimidine | 1.60(m, 2H), 2.75(q, 2H), 3.10(s, 3H), 3.25(m, 2H), 3.50(m, 4H), 3.60 (brs, 4H), 4.55(t, 1H), 7.35(t, 1H), 7.65(d, 2H), 7.75(brs, 1H), 7.90(d, 2H), 8.40(s, 1H) | 450 | Meth 4 |
| 121[1] | 5-Cyano-4-(2-hydroxyethylamino)-2-{4-[N-(3-methoxypropyl)sulphamoyl]anilino}pyrimidine | 1.55(m, 2H), 2.75(m 2H), 3.10(s, 3H), 3.25(m, 2H), 3.50(m, 2H), 3.60 (m, 2H), 4.75(t, 1H), 7.35(t, 1H), 7.65(d, 2H), 7.90(d, 2H), 8.40(s, 1H) | 406 | Meth 4 |

-continued

| Ex | Compound Name | NMR | m/z | SM |
|----|---------------|-----|-----|-----|
| 122 | 5-Cyano-4-(2-hydroxyethylamino)-2-(4-mesylanilino)pyrimidine | 3.12(s, 3H), 3.50(m, 2H), 3.60(m, 2H), 4.80(t, 1H), 7.70(t, 1H), 7.80(d, 2H), 8.00(d, 2H), 8.40(s, 1H) | 333 | Com Av |
| 123 | 5-Cyano-4-(isobutylamino)-2-(4-mesylanilino)pyrimidine | 0.95(d, 6H), 2.00(m, 1H), 3.25(m, 2H), 3.30(s, 3H), 7.80(d, 2H), 8.00 (d, 2H), 8.40(s, 1H), 10.25(s, 1H) | 345 | Com Av |
| 124 | 5-Cyano-4-(cyclopropylmethylamino)-2-(4-mesylanilino)pyrimidine | 0.30(m, 2H), 0.50(m, 2H), 1.20(m, 1H), 3.20(s, 3H), 3.35(m, 2H), 7.85 (d, 2H), 8.00(d, 3H), 8.45(s, 1H), 10.25(s, 1H) | 343 | Com Av |
| 125 | 5-Cyano-4-(cyclopropylamino)-2-{4-[N-(2,2,2-trifluoroethyl)sulphamoyl]anilino}pyrimidine | 0.65(m, 2H), 0.80(m, 2H), 2.85(m, 1H), 3.65(m, 2H), 7.70(d, 2H), 8.10 (d, 3H), 8.35(brs, 1H), 8.40(s, 1H) | 412 | Meth 9 |
| 126 | 5-Cyano-4-(ethylamino)-2-(4-ethylsulphonylanilino)pyrimidine | 1.10(t, 3H), 1.20(t, 3H), 3.20(m, 2H), 3.45(m, 2H), 7.80(d, 2H), 7.90 (m, 2H), 8.00(d, 2H), 8.40(s, 1H) | 331 | Ref[2] |
| 127 | 5-Cyano-4-(ethylamino)-2-{4-[N-(2,2,2-trifluoroethyl)sulphamoyl]anilino}pyrimidine | 1.20(t, 3H), 3.45(m, 2H), 3.65(m, 2H), 7.75(d, 2H), 7.85(t, 1H), 7.95 (d, 2H), 8.35(m, 2H) | 400 | Meth 9 |
| 128 | 5-Cyano-4-(methylamino)-2-(4-mesylanilino)pyrimidine | 2.90(d, 3H), 3.10(s, 3H), 7.80(d, 3H), 8.00(d, 2H), 8.40(s, 1H) | 303 | Com Av |
| 129 | 5-Cyano-4-(propylamino)-2-(4-mesylanilino)pyrimidine | 0.90(t, 3H), 1.60(m, 2H), 3.10(s, 3H), 3.40(m, 2H), 7.80(d, 2H), 7.90 (t, 1H), 8.00(d, 2H), 8.40(s, 1H) | 331 | Ref[2] |

[1]In this case the intermediate 2-anilino-4-phenoxy-5-cyanopyrimidine was isolated and purified before treatment with ethanolamine.
[2]Helv. Chim. Acta, 66(4) 1046–52(1983)

Example 130

5-Cyano-4-ethylamino-2-{4-[N-(2-hydroxy-3-piperidinopropyl)sulphamoyl]anilino}pyrimidine 4-[N-(2-Hydroxy-3-piperidinopropyl)sulphamoyl]aniline (Method 118; 200 mg, 0.64 mmol) was dissolved in methanol (4 ml). 1M Ethereal hydrogen chloride (1.28 ml, 1.28 mmol) was added and the mixture gently warmed to give a solution. The volatiles were partially evaporated to give a volume of approx. 1.5 ml. 2-Butanol (5 ml) was added and the cloudy solution warmed to 50° C. 2-Chloro-5-cyano-4-ethylaminopyrimidine (Method 56; 233 mg, 1.28 mmol) was added in portions and the reaction was then heated at 95° C. for 20 hours. The hot supernatant was decanted from the solid residue and the solution allowed to cool. The resulting precipitate was collected by filtration, washed with diethyl ether and suspended in water (approx. 35 ml). The suspension was adjusted to pH>10 with 2M aqueous sodium hydroxide solution and extracted with ethyl acetate (3×15 ml). The extracts were dried, the volatiles evaporated and the residue purified by chromatography on silica eluting with DCM/methanolic ammonia (100:0) increasing in polarity to (85:15). The product was triturated with diethyl ether and collected by filtration to give the title compound (30 mg, 10%). NMR: 1.15 (t, 3H), 1.35 (m, 2H), 1.43 (m, 4H), 2.10–2.35 (m, 6H), 2.68 (m, 1H), 2.83 (m, 1H), 3.48 (quin, 2H), 3.56 (m, 1H), 4.59 (s, 1H) 7.36 (brt, 1H), 7.70 (d, 2H), 7.88 (t, 1H), 7.95 (d, 2H), 8.40 (s, 1H) 10.16 (s, 1H); m/z: 460.

Examples 131–132

The following compounds were prepared starting from 4-[N-(2-hydroxy-3-piperidinopropyl)sulphamoyl]aniline (Method 118) using the procedure of Example 130 and the appropriate pyrimidine starting material.

| Ex | Compound Name | NMR | m/z | SM |
|----|---------------|-----|-----|-----|
| 131 | 5-Cyano-4-cyclopropylamino-2-{4-[N-(2-hydroxy-3-piperidinopropyl)sulphamoyl]anilino}pyrimidine | 0.70(m, 2H), 0.84(m, 2H), 1.30–1.52 (m, 6H), 2.10–2.30(m, 6H), 2.67(m, 1H), 2.90(m, 2H), 3.58(m, 1H), 4.60 (brs, 1H), 7.37(t, 1H) 7.70(d, 2H), 8.05 (d, 3H), 8.40(s, 1H), 10.23(brs, 1H) | 472 | Meth 96 |
| 132 | 5-Cyano-4-(2,2,2-trifluoroethylamino)-2-{4-[N-(2-hydroxy-3-piperidinopropyl)sulphamoyl]anilino}pyrimidine | 1.25–1.85(m, 6H), 2.10–2.80(m, 8H), 3.80(brs, 1H), 4.25(m, 2H), 4.60(brs, 1H), 7.60(brs, 1H), 7.71(d, 2H), 7.91 (d, 2H), 8.42(t, 1H), 8.55(s, 1H), 10.35 (brs, 1H) | 514 | Meth 95 |

Preparation of Starting Materials

The starting materials for the above Examples are either commercially available or are readily prepared by standard methods from known materials. For example the following reactions are illustrations but not limitations of the preparation of some of the starting materials used in the above reactions.

Method 1

4-[N-(3-Isopropylaminopropyl)sulphamoyl]aniline.

Sulphanilyl fluoride (6.5 g, 37.1 mmol), N-isopropyl-1,3-propanediamine (5.71 ml, 40.8 mmol) and triethylamine (5.69 ml, 40.8 mmol) in N-butanol (15 ml) was heated at reflux for 10 hours. The mixture was allowed to cool, silica was added and the volatiles were evaporated. The residue was purified by chromatography eluting with DCM/methanolic ammonia (100:0) increasing in polarity to (90:10) to give the title compound as a clear oil which crystallized on standing (8.81 g, 88%). NMR: 0.89 (d, 6H), 1.43 (m, 2H), 2.41 (t, 2H), 2.58 (m, 1H), 2.68 (t, 2H), 3.16 (s, 2H), 5.85 (s, 2H), 6.58 (d, 2H), 7.38 (d, 2H); m/z: 272.

Methods 2–9

The following compounds were prepared using the procedure of Method 1.

| Meth | Compound Name | m/z |
|---|---|---|
| 2 | 4-[N-(tetrahydrofur-2-ylmethyl)sulphamoyl]aniline | 257 |

| Meth | Compound Name | NMR | m/z |
|---|---|---|---|
| 3 | 4-[N-(3-hydroxy-2,2-dimethylpropyl)sulphamoyl]aniline | 0.72(s, 6H), 2.45(d, 2H), 3.06(d, 2H), 4.37(t, 1H), 5.83(s, 2H), 6.57(d, 2H), 6.85 (t, 1H), 7.40(d, 2H) | 259 |
| 4 | 4-[N-(3-methoxypropyl)sulphamoyl]aniline | 1.60(m, 2H), 2.95(q, 2H), 3.20(s, 3H), 3.30(t, 2H), 4.10(brs, 2H), 4.90(brt, 1H), 6.60(d, 2H), 7.55(d, 2H) | 244 |
| 5 | 4-[N-(2-methoxyethyl)sulphamoyl]aniline | 2.80(q, 2H), 3.15(s, 3H), 3.30(t, 2H), 5.85 (brs, 2H), 6.60(d, 2H), 7.10(t, 1H), 7.40 (d, 2H) | 230 |
| 6 | 4-(N-allylsulphamoyl)aniline | 3.30(t, 2H), 5.00(d, 1H), 5.10(d, 1H), 5.65 (m, 1H), 5.85(s, 2H), 6.40(d, 2H), 7.20(t, 1H), 7.40(d, 2H) | 212 |
| 7 | 4-[N-(2-piperidinoethyl)sulphamoyl]aniline | 1.30(brm, 2H), 1.40(brm, 4H), 2.25(brm, 6H), 2.70(brt, 2H), 5.85(s, 2H), 6.60(d, 2H), 6.80(brs, 1H), 7.40(d, 2H) | 283 |
| 8 | 4-(N-n-pentylsulphamoyl)aniline | 0.80(t, 3H), 1.20(brm, 4H), 1.35(brm, 2H), 2.80(q, 2H), 4.10(brs, 2H), 4.40(t, 1H), 6.60(d, 2H), 7.45(d, 2H) | 242 |
| 9 | 4-[N-(2,2,2-trifluoroethyl)sulphamoyl]aniline | 3.50(m, 2H), 5.90(brs, 2H), 6.60(d, 2H), 7.40(d, 2H), 8.00(brt, 1H) | 254 |

Method 10

N-(2-Methoxyethyl)-N-methyl-4-nitrobenzenesulphonamide

A stirred solution of triethylamine (2.4 ml, 17.23 mmol) and N-(2-methoxyethyl)methylamine (1.5 g, 16.85 mmol) in DCM (20 ml) was cooled in an ice/water bath. A solution of 4-nitrobenzenesulphonyl chloride (3.2 g, 14.45 mmol) in DCM (20 ml) was added dropwise. The reaction was stirred for one hour the cooling bath was removed and the mixture stirred for further 3 hours. The reaction mixture was washed with 1M hydrochloric acid (40 ml), water (30 ml) and then brine. The volatiles were evaporated to give the title compound (3.8 g). M/z: 245.

Methods 11–14

Using the procedure of Method 10 starting from 4-nitrobenzenesulphonyl chloride and the appropriate commercially available amine the following compounds were prepared.

| Meth | Compound Name | m/z |
|---|---|---|
| 11 | N-(2-Diethylaminoethyl)-4-nitrobenzenesulphonamide | 302 |
| 12 | N-(2-Diethylaminoethyl)-N-methyl-4-nitrobenzenesulphonamide | 316 |

| Meth | Compound Name | NMR | m/z |
|---|---|---|---|
| 13 | 4-Nitro-N-(2-piperidinoethyl)benzenesulphonamide | 1.35(brs, 1H), 1.72(brm, 5H), 2.85(brs, 2H), 3.09(brt, 2H), 3.26(brq, 2H), 3.35(brm, 2H), 8.10(d, 2H), 8.41(d, 2H), 8.55(brt, 1H) | 314 |

| | -continued | | |
|---|---|---|---|
| 14 | 4-Nitro-N-(3-piperidinopropyl)benzenesulphonamide | 1.33(brt, 2H), 1.40(m, 4H), 1.51(m, 2H), 2.18(brt, 6H), 2.82(t, 2H), 8.02(d, 2H), 8.41 (d, 2H) | 328 |

Method 15
N-Methyl-4-nitro-N-(3-piperidinopropyl)benzenesulphonamide

4-Nitro-N-(3-piperidinopropyl)benzenesulphonamide (Method 14; 1 g, 3.06 mmol) was stirred under nitrogen at ambient temperature. Sodium hydride (60% dispersion in mineral oil) (122 mg, 3.05 mmol) was added in portions. The reaction was stirred for 10 minutes, then iodomethane (210 μl, 3.38 mmol) was added dropwise. After 2 hours, added extra sodium hydride (<30 mg) was added, and the reaction was stirred for 15 minutes, then stood overnight. Volatiles were removed by evaporation, water (20 ml) was added and the solution was extracted with ethyl acetate (2×30 ml). The organic layers were combined, washed with water and the volatiles evaporated to give the title compound (830 mg). NMR: 1.34 (m, 2H), 1.45 (m, 4H), 1.60 (quintet, 2H), 2.19 (m, 2H), 2.24 (m, 4H), 2.72 (s, 3H), 3.02 (t, 2H), 8.02 (d, 2H), 8.40 (d, 2H); m/z: 342.

Method 16
4-[N-(2-Methoxyethyl)-N-(methyl)sulphamoyl]aniline

N-(2-Methoxyethyl)-N-methyl-4-nitrobenzenesulphonamide (Method 10; 3.88 g) was reduced by hydrogenation in ethanol (100 ml) over 10% palladium on carbon (400 mg) at 3 bar pressure. The catalyst was removed by filtration and the volatiles evaporated to give the title compound (3.2 g). M/z: 245.

Methods 17–20
The following compounds were prepared using the procedure of Method 16.

| Meth | Compound Name | m/z | SM |
|---|---|---|---|
| 17 | 4-[N-(2-Diethylaminoethyl)sulphamoyl]aniline | 272 | Meth 11 |
| 18 | 4-[N-(2-Diethylaminoethyl)-N-(methyl)sulphamoyl]aniline | 286 | Meth 12 |
| 19[1] | 4-[N-(3-Piperidinopropyl)sulphamoyl]aniline(hydrochloride) | 298 | Meth 14 |
| 20[1] | 4-[N-(Methyl)-N-(3-piperidinopropyl)sulphamoyl]aniline(hydrochloride) | 312 | Meth 15 |

[1]Reduced in 1M hydrochloric acid/ethanol

Method 21
1Nitro-4-[4-(phthalimido)butylsulphide]phenyl

4-Nitrothiophenol (1.9 g, 12.26 mmol) was stirred in DMF under nitrogen and cooled (ice/water bath). Sodium hydride (60% dispersion in oil: 400 mg, 10 mmol) was added in portions and the mixture stirred for 10 minutes. N-(4-bromobutyl)phthalimide (2.8 g, 9.93 mmol) in DMF (10 ml) was added and the reaction was heated at 90° C. for 1.5 hours, cooled to room temperature and stood overnight at ambient temperature. Volatiles were removed by evaporation, water (20 ml) was added and the solution was extracted into ethyl acetate (50+25 ml). The organic layers were combined, washed with water (20 ml) and brine, dried and the volatiles evaporated. The resulting gum was triturated twice with isohexane. The solvent was decantated to give the title compound as a solid (3.8 g). NMR: 1.64 (m, 2H), 1.74 (m, 2H), 3.12 (t, 2H), 3.60 (t, 2H), 7.45 (d, 2H), 7.81 (m, 4H), 8.06 (d, 2H).

Method 22
The following compound was prepared using the procedure of Method 21

| Meth | Compound Name | NMR | M/z |
|---|---|---|---|
| 22 | 1-Nitro-4-[3-(phthalimido)propylsulphide]phenyl | 1.97 (quin, 2H), 3.18 (t, 2H), 3.71 (t, 2H), 7.49 (d, 2H), 7.71 (m, 4H), 8.10 (d, 2H) | 342 (EI) |

Method 23
1-Nitro-4-[4-(phthalimido)butylsulphonyl]phenyl

A solution of chromium(VI)oxide (3.5 g, 35.0 mmol) in water (3 ml) and glacial acetic acid (12.5 ml) was added dropwise over 15 to 20 minutes to a solution of 1-nitro-4-[4-(phthalimido)butylsulphide]phenyl (Method 21; 3.5 g, 9.83 mmol) in glacial acetic acid (17.5 ml) heated at 90–100° C. The mixture was then heated at 100° C. for 3.5 hours. The reaction was cooled and poured onto crushed ice (250 g). The solid was collected by filtration and washed with water. The solid was dried by azeotroping with methanol 3 times to give the title compound (3.4 g). M/z: 389.

Method 24
1-Nitro-4-[3-(phthalimido)propylsulphonyl]phenyl

1-Nitro-4-[3-(phthalimido)propylsulphide]phenyl (Method 22; 600 mg) was dissolved in DCM (20 ml) and methanol (1 ml). 3-Chloroperbenzoic acid (70%; 1.4 g) was added in portions over 10 minutes. After 75 minutes DCM (10 ml), saturated sodium bicarbonate solution (10 ml) and water (10 ml) was added and the solution was stirred for 20 minutes before additional saturated sodium. T and the organic layer was separated and washed with water and brine, dried and evaporated to dryness to give the title compound (795 mg). NMR: 1.90 (m, 2H), 3.55 (m, 2H), 3.64 (t, 2H), 7.81 (s, 4H), 8.17 (d, 2H), 8.41 (d, 2H)

Method 25
1-Nitro-4-(4-aminobutylsulphonyl)phenyl

1-Nitro-4-[4-(phthalimido)butylsulphonyl]phenyl (Method 23; 3 g, 7.73 mmol) was heated at 90° C. in acetonitrile (30 ml) and methanol (10 ml). Hydrazine hydrate (0.76 ml, 15.7 mmol) was added and the reaction was heated for 1.5 hours, then cooled, and stood overnight at ambient temperature. The resulting solid was removed by filtration and washed with methanol. The combined filtrates were evaporated to give the title compound (2.3 g). M/z: 259.

Method 26
4-(3-Aminopropyl-sulphonyl)-1-nitrophenyl

The title compound was prepared from Method 24 using the procedure of Method 25.

Method 27
1-Nitro-4-[4-(isopropylamino)butylsulphonyl]phenyl

1-Nitro-4-(4-aminobutylsulphonyl)phenyl (Method 25; 2 g, 7.75 mmol) was stirred in methanol (20 ml) and acetone (2.3 ml) was added. Sodium cyanoborohydride (730 mg, 11.62 mmol) was added in portions over 5 minutes and the reaction was stirred for 2.5 hours. Water (15 ml) was added, and the organic solvents were removed by evaporation more water was added and the solution was extracted with ethyl acetate (130 ml). The organic layers were washed with water (25 ml) and brine. The volatiles were evaporated and the residue was purified by chromatography on neutral alumina (activity II), eluting with DCM increasing polarity to methanol: DCM (3:97) to give the title compound (1.26 g). m/z: 301.

Method 28

The following compound was prepared using the procedure of Method 27.

| Meth | Compound Name | NMR | m/z | SM |
|---|---|---|---|---|
| 28 | 4-[3-(Isopropylamino) propylsulphonyl]-1-nitrophenyl | 1.08 (d, 6H), 1.96 (quin, 2H), 2.77 (m, 2H), 2.81 (m, 1H), 3.30 (m, 2H), 8.12 (d, 2H), 8.39 (d, 2H) | 287 | Meth 26 |

Method 29

4-[4-(Isopropylamino)butylsulphonyl]aniline

1-Nitro-4-[4-(isopropylamino)butylsulphonyl]phenyl (Method 27; 1.2 g, 4 mmol) was dissolved in ethanol (20 ml) and 1M hydrochloric acid (6 ml) and hydrogenated at 1 atmosphere over 10% palladium on carbon (400 mg) for 4 hours at 1 atmosphere. The catalyst was removed by filtration and the volatiles evaporated to give the title compound as a foam. M/z: 271.

Method 30

The following compound was prepared using the procedure of Method 29.

| Meth | Compound Name | NMR | m/z | SM |
|---|---|---|---|---|
| 30 | 4-[3-(Isopropylamino) propylsulphonyl] | 1.19 (d, 6H), 1.89 (quintet, 2H), 2.89 | 257 | Meth 28 |

| Meth | Compound Name | NMR | m/z | SM |
|---|---|---|---|---|
| | aniline | (m, 2H), 3.28 (t, 2H), 6.70 (d, 2H), 7.48 (d, 2H), 9.00 (brs, 2H) | | |

Method 31

2,4-Dichloro-5-chloroformylpyrimidine

5-Carboxy-2,4-dihydroxypyrimidine (19.0 g, 0.12 mol), phosphorus pentachloride (83.5 g, 0.40 mol); and phosphoryl chloride (28.3 ml, 0.30 mol) were heated at 114° C. for 5 hours. The resulting solution was cooled overnight and the volatiles removed by evaporation. The residue was purified by vacuum distillation to yield the title compound as a clear oil (17.85 g, 70%). M/z: 211.

Method 32

5-N-t-Butylcarbamoyl-2-chloro-4-morpholinopyrimidine.

A solution of 2,4-dichloro-5-chloroformylpyrimidine (Method 31; 500 mg, 2.36 mmol) in dry THF (5 ml) was cooled to −15° C. t-Butylamine (250□l, 2.36 mmol) and triethylamine (330□l, 2.36 mmol) in dry THF were added slowly so as to maintain the temperature below −10° C. The resulting mixture was stirred at −10° C. for 2 hours, allowed to warm to ambient temperature and stirred for a further 30 minutes. Morpholine (208□l, 2.36 mmol) and triethylamine (330□l, 2.36 mmol) in dry THF (1 ml) were added and the resulting mixture was stirred at room temperature for 12 hours. The precipitate was removed by filtration and the filtrate evaporated to give the title compound as a pale yellow solid (570 mg, 78%). NMR: 1.30 (s, 9H), 3.52–3.58 (m, 4H), 3.60–3.67 (m, 4H), 8.00 (s, 1H), 8.21 (brs, 1H); m/z: 299.

Methods 33–54

The following intermediates were prepared using the procedure of Method 32 starting from 2,4-dichloro-5-chloroformylpyrimidine (Method 31), t-butyl amine and amines.

| Meth | Compound Name | m/z |
|---|---|---|
| 33[1] | 5-N-t-Butylcarbamoyl-2-chloro-4-(2-methylpropylamino)pyrimidine | 285 |
| 34[1] | 5-N-t-Butylcarbamoyl-2-chloro-4-ethylaminopyrimidine | 257 |
| 35[1] | 5-N-t-butylcarbamoyl-2-chloro-4-(2-fluoroethylamino)pyrimidine | 273 |
| 36[1] | 5-N-t-butylcarbamoyl-2-chloro-4-(3-ethoxypropylamino)pyrimidine | 315 |
| 37[1] | 5-N-t-butylcarbamoyl-2-chloro-4-n-butylaminopyrimidine | 285 |
| 38[1] | 5-N-t-butylcarbamoyl-2-chloro-4-[N-(methyl)allylamino]pyrimidine | 283 |
| 39[1] | 5-N-t-butylcarbamoyl-2-chloro-4-[N-(methyl)-ethoxycarbonylmethylamino]pyrimidine | 329 |
| 40[1] | 5-N-t-butylcarbamoyl-2-chloro-4-[N-(methyl)-2-cyanoethylamino]pyrimidine | 296 |
| 41[1] | 5-N-t-butylcarbamoyl-2-chloro-4-diethylaminopyrimidine | 285 |
| 42[1] | 5-N-t-butylcarbamoyl-2-chloro-4-[N-(methyl)-2-methoxyethylamino]pyrimidine | 301 |
| 43 | 5-N-t-butylcarbamoyl-2-chloro-4-(2,2,2-trifluoroethylamino)pyrimidine | 311 |
| 44 | 5-N-t-butylcarbamoyl-2-chloro-4-[bis-(2-cyanoethyl)amino]pyrimidine | 335 |
| 45 | 5-N-t-butylcarbamoyl-2-chloro-4-(3-morpholinopropylamino)pyrimidine | 356 |
| 46 | 5-N-t-butylcarbamoyl-2-chloro-4-(cyclopropylamino)pyrimidine | 269 |
| 47 | 5-N-t-butylcarbamoyl-2-chloro-4-(cyclopropylmethylamino)pyrimidine | 283 |
| 48 | 5-N-t-butylcarbamoyl-2-chloro-4-(cyclohexylamino)pyrimidine | 311 |
| 49 | 5-N-t-butylcarbamoyl-2-chloro-4-(tetrahydrofur-2-ylmethylamino)pyrimidine | 2 |
| 50 | 5-N-t-butylcarbamoyl-2-chloro-4-(pyrid-3-ymethylamino)pyrimidine | 320 |
| 51 | 5-N-t-butylcarbamoyl-2-chloro-4-piperidinopyrimidine | 297 |
| 52 | 5-N-t-butylcarbamoyl-2-chloro-4-[N-(ethyl)-cyclohexylamino]pyrimidine | 339 |
| 53 | 5-N-t-butylcarbamoyl-2-chloro-4-(ethoxycarbonylmethylamino)pyrimidine | 315 |
| 54 | 5-N-t-butylcarbamoyl-2-chloro-4-(2-methoxycarbonylethylamino)pyrimidine | 315 |

[1]Products were purified by chromatography eluting with DCM/methanol (100:0) increasing in polarity to (95:5).

| Meth | Compound Name | m/z |
|---|---|---|

[2]NMR: 1.35 (s, 9H); 2.5 (m, 2H); 1.8 (m, 2H), 3.35 (m, 1H), 3.54 (m, 1H), 3.65 (m, 1H), 3.77 (m, 1H), 4.0 (m, 1H), 7.95 (s, 1H) 8.48 (s, 1H), 9.96 (m, 1H).

Method 55
2-Chloro-5-cyano-4-morpholinopyrimidine

5-N-t-Butylcarbamoyl-2-chloro-4-morpholinopyrimidine (Method 32; 560 mg, 1.88 mmol) in thionyl chloride (4 ml) was heated at 90° C. for 2 hours. The mixture was cooled to room temperature and the volatiles evaporated, and the residue azeotroped with toluene, to yield the title compound as a brown solid (425 mg). NMR: 3.66–3.74 (m, 4H), 3.85–3.93 (m, 4H), 8.63 (s, 1H); m/z: 225, 227.

Method 56
2-Chloro-5-cyano-4-ethylaminopyrimidine.

5-N-t-Butylcarbamoyl-2-chloro-4-ethylaminopyrimidine (Method 34; 255 mg, 1.00 mmol) and thionyl chloride (240 μl, 3.29 mmol) in toluene (2 ml) was heated at 90° C. for 15 hours. The mixtures were allowed to cool to room temperature, silica was added and the volatiles were evaporated. The residue was purified by chromatography eluting with DCM/methanol (100:0) increasing in polarity to (97:3) to give the title compound (86 mg). NMR: 1.12 (t, 3H), 3.39 (m, 2H), 8.52 (s, 1H), 8.55 (brs, 1H).

Methods 57–66

The following compounds were prepared using the procedure of Method 56 from the appropriate pyrimidine starting material.

| Meth | Compound Name | NMR | m/z | SM |
|---|---|---|---|---|
| 57 | 2-Chloro-5-cyano-4-(2-methylpropylamino)pyrimidine | 0.86 (d, 6H), 1.93 (m, 1H), 3.18 (t, 2H), 8.51 (s, 1H), 8.58 (brs, 1H) | 211 | Meth 33 |
| 58 | 2-Chloro-5-cyano-4-(2-fluoroethylamino)pyrimidine | 3.64 (bt, 1H), 3.73 (bt, 1H), 4.49 (t, 1H), 4.64 (t, 1H), 8.57 (s, 1H), 8.70 (brs, 1H) | | Meth 35 |
| 59 | 2-Chloro-5-cyano-4-(3-ethoxypropylamino)pyrimidine | 1.09 (t, 3H), 1.77 (m, 2H), 3.34–3.48 (m, 6H), 8.46 (brs, 1H), 8.53 (s, 1H) | | Meth 36 |
| 60 | 2-Chloro-5-cyano-4-n-butylaminopyrimidine | 0.89 (t, 3H), 1.29 (m, 2H), 1.51 (m, 2H), 3.36 (m, 2H), 8.51 (s, 1H), 8.54 (brs, 1H) | 209 (MH)- | Meth 37 |
| 61 | 2-Chloro-5-cyano-4-[N-(methyl)allylamino]pyrimidine | 3.25 (s, 3H), 4.33 (d, 2H), 5.20 (m, 2H), 5.85 (m, 1H), 8.59 (s, 1H) | | Meth 38 |
| 62 | 2-Chloro-5-cyano-4-[N-(methyl)-ethoxycarbonylmethylamino]pyrimidine | 1.19 (t, 3H), 3.27 (s, 3H), 4.16 (q, 2H), 4.51 (brs, 2H), 8.68 (s, 1H) | | Meth 39 |
| 63 | 2-Chloro-5-cyano-4-[N-(methyl)-2-cyanoethylamino]pyrimidine | 2.90 (t, 2H), 3.38 (s, 3H), 3.97 (t, 2H), 8.66 (s, 1H) | 222 | Meth 40 |
| 64 | 2-Chloro-5-cyano-4-diethylaminopyrimidine | 1.19 (t, 6H), 3.69 (q, 4H), 8.57 (s, 1H) | | Meth 41 |
| 65 | 2-Chloro-5-cyano-4-[N-(methyl)-2-methoxyethylamino]pyrimidine | 3.26 (s, 3H), 3.32 (s, 3H), 3.57 (t, 2H), 3.90 (t, 2H), 8.59 (s, 1H) | | Meth 42 |
| 66[1] | 2-Chloro-5-cyano-4-(3-morpholinopropylamino)pyrimidine | | 282 | Meth 45 |

[1]Prepared by the procedure of Method 55.

Method 67
4-n-Butylamino-5-N-t-butylcarbamoyl-2-{4-[N-(tetrahydrofur-2-ylmethyl)sulphamoyl]anilino}pyrimidine 4-n-Butylamino-5-N-t-butylcarbamoyl-2-chloropyrimidine (Method 37; 282 mg, 1.0 mmol), 4-[N-(tetrahydrofur-2-ylmethyl)sulphamoyl]aniline (Method 2; 241 mg, 0.95 mmol) and 1M ethereal hydrogen chloride (993 μl, 1.0 mmol) in 2-butanol (2 ml) were heated at 90° C. for 3 hours. The mixture was cooled, silica was added and the volatiles were evaporated. The residue was purified by chromatography eluting with DCM/methanol (100:0) increasing in polarity to (95:5) to give the title compound as a white solid (372 mg). M/z: 505.

Methods 68–78

The following examples were all prepared using the procedure of Method 67 from 4-[N-(tetrahydrofur-2-ylmethyl)sulphamoyl]aniline (Method 2) and the appropriate pyrimidine.

| Meth | Compound | m/z | SM |
|---|---|---|---|
| 68[1] | 5-N-t-Butylcarbamoyl-2-{4-[N-(tetrahydrofur-2-ylmethyl) sulphamoyl]anilino}-4-(2,2,2-trifluoroethylamino)pyrimidine | 531 | Meth 43 |
| 69 | 4-[Bis-(2-cyanoethyl)amino]-5-N-t-butylcarbamoyl-2-{4-[N-(tetrahydrofur-2-ylmethyl)sulphamoyl]anilino}pyrimidine | 555 | Meth 44 |
| 70 | 4-(Cyclopropylamino)-5-N-t-butylcarbamoyl-2-{4-[N-(tetrahydrofur-2-ylmethyl)sulphamoyl]anilino}pyrimidine | 489 | Meth 46 |
| 71 | 4-(Cyclopropylmethylamino)-5-N-t-butylcarbamoyl-2-{4-[N-(tetrahydrofur-2-ylmethyl)sulphamoyl]anilino}pyrimidine | 503 | Meth 47 |
| 72 | 4-(Cyclohexylamino)-5-N-t-butylcarbamoyl-2-{4-[N-(tetrahydrofur-2-ylmethyl)sulphamoyl]anilino}pyrimidine | 531 | Meth 48 |
| 73 | 5-N-t-Butylcarbamoyl-2-{4-[N-(tetrahydrofur-2-ylmethyl) sulphamoyl]anilino}-4-(tetrahydrofur-2-ylmethylamino)pyrimidine | 533 | Meth 49 |
| 74 | 5-N-t-Butylcarbamoyl-4-(pyrid-3-ylmethylamino)-2-{4-[N-(tetrahydrofur-2-ylmethyl)sulphamoyl]anilino}pyrimidine | 540 | Meth 50 |
| 75 | 5-N-t-Butylcarbamoyl-4-(piperidino)-2-{4-[N-(tetrahydrofur-2-ylmethyl)sulphamoyl]anilino}pyrimidine | 517 | Meth 51 |
| 76 | 5-N-t-Butylcarbamoyl-4-[N-(ethyl)cyclohexylamino]-2-{4-[N-(tetrahydrofur-2-ylmethyl)sulphamoyl]anilino}pyrimidine | 559 | Meth 52 |
| 77[2] | 4-(N-Butoxycarbonylmethylamino)-5-N-t-butylcarbamoyl-2-{4-[N-(tetrahydrofur-2-ylmethyl)sulphamoyl]anilino}pyrimidine | 563 | Meth 53 |
| 78 | 5-N-t-Butylcarbamoyl-4-(2-methoxycarbonylethylamino)-2-{4-[N-(tetrahydrofur-2-ylmethyl)sulphamoyl]anilino}pyrimidine | 535 | Meth 54 |

[1]Chromatography eluent was isohexane/ethyl acetate (100:0) increasing in polarity to (50:50).
[2]Ester exchange occurred.

Method 79

5-N-t-Butylcarbamoyl-2,4-dichloropyrimidine.

A solution of 2,4-dichloro-5-chloroformylpyrimidine (Method 31; 9.8 g, 46.3 mmol) in dry THF (50 ml) was cooled to −15° C. t-Butylamine (5.2 ml, 49.3 mmol) and triethylamine (6.9 ml, 49.5 mmol) in dry THF (20 ml) were added slowly so as to maintain the temperature below −10° C. The resulting mixture was stirred at −10° C. for 2 hours, allowed to warm to ambient temperature and stirred for a further 30 minutes. The precipitate was removed by filtration and the filtrate evaporated to give a viscous oil, and then evaporated under high vacuum to give the title compound as a solid (10.48 g, 90%). NMR: 1.49 (s, 9H), 6.19 (brs, 1H), 8.86 (s, 1H); m/z: 248.

Method 80

5-N-t-Butylcarbamoyl-2-chloro-4-[4-(2-hydroxyethyl)piperazin-1-yl]pyrimidine.

A solution of triethylamine (210 μl, 1.5 mmol) and 1-(2-hydroxyethyl)piperazine (195 mg, 1.5 mmol) in dry THF (3 ml) was added to a solution of 5-N-t-butylcarbamoyl-2,4-dichloropyrimidine (Method 79; 372 mg, 1.5 mmol) in dry THF (2 ml). The mixture was stirred at ambient temperature for 5 hours. The resulting precipitate was removed by filtration, the filter pad washed with dry ether (5 ml) and the filtrate evaporated to give the title compound. M/z: 342 (1×Cl).

Methods 81–94

The following derivatives were prepared from 5-N-t-butylcarbamoyl-2,4-dichloropyrimidine (Method 79) and the appropriate amine using the procedure of Method 80.

| Meth | Compound Name | m/z |
|---|---|---|
| 81 | 5-N-t-Butylcarbamoyl-2-chloro-4-(2-dimethylaminoethylamino)pyrimidine | 300 |
| 82 | 5-N-t-Butylcarbamoyl-2-chloro-4-(2,6-dimethylmorpholino)pyrimidine | 327 |
| 83 | 5-N-t-Butylcarbamoyl-2-chloro-4-(cis-2,6-dimethylmorpholino)pyrimidine | 327 |
| 84 | 5-N-t-Butylcarbamoyl-2-chloro-4-(cyanomethylamino)pyrimidine | 268 |
| 85 | 5-N-t-Butylcarbamoyl-2-chloro-4-(3,5-dimethylpiperidino)pyrimidine | 325 |
| 86 | 5-N-t-Butylcarbamoyl-2-chloro-4-[4-(2-methoxyethyl)piperazin-1-yl]pyrimidine | 356 |
| 87 | 5-N-t-Butylcarbamoyl-2-chloro-4-(4-methylpiperazin-1-yl)pyrimidine | 312 |
| 88 | 5-N-t-Butylcarbamoyl-2-chloro-4-(4-isopropylpiperazin-1-yl)pyrimidine | 340 |
| 89 | 5-N-t-Butylcarbamoyl-2-chloro-4-[4-(ethylsulphonyl)piperazin-1-yl]pyrimidine | 390 |
| 90 | 5-N-t-Butylcarbamoyl-4-(ethoxycarbonylpiperazin-1-yl)-2-chloropyrimidine | 369 |
| 91 | 5-N-t-Butylcarbamoyl-2-chloro-4-methylaminopyrimidine | 243 |
| 92 | 5-N-t-Butylcarbamoyl-2-chloro-4-(2-propynylamino)pyrimidine | 267 |
| 93[1] | 5-N-t-Butylcarbamoyl-2-chloro-4-[N-(methyl)-2,2,2-trifluoroethylamino]pyrimidine | 325 |
| 94 | 5-N-t-Butylcarbamoyl-2-chloro-4-(2-methoxyethylamino)pyrimidine | 287 |

[1]Purified by chromatography eluting with DCM/MeOH (98:2).

Method 95

2-Chloro-5-cyano-4-(2,2,2-trifluoroethylamino)pyrimidine

A solution of 5-N-t-butylcarbamoyl-2-chloro-4-(2,2,2-trifluoroethylamino)pyrimidine (Method 43; 8.5 g, 0.027 mol) in thionyl chloride (100 ml) was heated at reflux for 4 hours. The thionyl chloride was removed by evaporation and the resulting gum was triturated with isohexane/ethyl acetate (95/5), collected by filtration and dried to give the title compound NMR: 4.20 (m, 2H), 8.70 (s, 1H), 9.10 (brt, 1H); m/z: 236

Method 96
2-Chloro-5-cyano-4-cyclopropylaminopyrimidine

5-N-t-Butylcarbamoyl-2-chloro-4-cyclopropylaminopyrimidine (Method 46; 2.40 g, 8.92 mmol) was heated at 80–90° C. with thionyl chloride (10 ml) for 4–6 hours. The thionyl chloride was removed by evaporation, and the residue triturated with ether/ethyl acetate to give the title compound (2.00 g), which was used without further purification.

Methods 97–110

The following compounds were prepared using the procedure of Method 96 from the appropriate pyrimidine starting material. Final products were not characterised but were used immediately in subsequent reactions.

| Meth | Compound Name | SM |
|------|---------------|-----|
| 97 | 2-Chloro-5-cyano-4-(2-dimethylaminoethylamino)pyrimidine | Meth 81 |
| 98 | 2-Chloro-5-cyano-4-(2,6-dimethylmorpholino)pyrimidine | Meth 82 |
| 99 | 2-Chloro-5-cyano-4-(cis-2,6-dimethylmorpholino)pyrimidine | Meth 83 |
| 100 | 2-Chloro-5-cyano-4-(cyanomethylamino)pyrimidine | Meth 84 |
| 101 | 2-Chloro-5-cyano-4-(3,5-dimethylpiperidino)pyrimidine | Meth 85 |
| 102 | 2-Chloro-5-cyano-4-[4-(2-methoxyethyl)piperazin-1-yl]pyrimidine | Meth 86 |
| 103 | 2-Chloro-5-cyano-4-(4-methylpiperazin-1-yl)pyrimidine | Meth 87 |
| 104 | 2-Chloro-5-cyano-4-(4-isopropylpiperazin-1-yl)pyrimidine | Meth 88 |
| 105 | 2-Chloro-5-cyano-4-[(4-ethylsulphonyl)piperazin-1-yl]pyrimidine | Meth 89 |
| 106 | 2-Chloro-4-(4-ethoxycarbonylpiperazin-1-yl)-5-cyanopyrimidine | Meth 90 |
| 107 | 2-Chloro-5-cyano-4-methylaminopyrimidine | Meth 91 |
| 108 | 2-Chloro-5-cyano-4-(2-propynylamino)pyrimidine | Meth 92 |
| 109 | 2-Chloro-5-cyano-4-[N-(methyl)-2,2,2-trifluoroethylamino]pyrimidine | Meth 93 |
| 110 | 2-Chloro-5-cyano-4-(2-methoxyethylamino)pyrimidine | Meth 94 |

Method 111
5-Cyano-4-ethylamino-2-[4-(fluorosulphonyl)anilino]pyrimidine

2-Chloro-5-cyano-4-ethylaminopyrimidine (Method 56; 6.35 g, 34.88 mmol) and sulphanilyl fluoride (6.11 g, 34.88 mmol) in 2-butanol (120 ml) were heated at 95° C. for 4 hours and then stirred at ambient temperatures for 48 hours. The volatiles were evaporated and the residue triturated with ether to give the title compound (10.46 g, 93%). NMR: 1.20 (t, 3H), 3.45 (m, 2H), 8.00 (d, 2H), 8.13 (d, 2H), 8.41 (s, 1H), 10.52 (s, 1H); m/z: 321.

Method 112–113

The following compounds were prepared using the procedure of Method 111 from the appropriate pyrimidine starting material.

| Meth | Compound Name | NMR | m/z | SM |
|------|---------------|-----|-----|-----|
| 112 | 5-Cyano-4-n-butylamino-2-[4-(fluorosulphonyl)anilino]pyrimidine | 0.9 (t, 3H), 1.35 (m, 2H), 1.6 (m, 2H), 3.42 (m, 2H), 8.00 (d, 2H), 8.14 (d, 2H), 8.50 (s, 1H), 10.6 (s, 1H), 10.87 (brs, 1H) | 349 | Meth 60 |
| 113 | 5-Cyano-4-(2,2,2-trifluoroethylamino)-2-[4-(fluorosulphonyl)anilino]pyrimidine | 4.24 (m, 2H), 8.0 (d, 2H), 8.08 (d, 2H), 8.49 (t, 1H), 8.58 (s, 1H), 10.62 (brs, 1H) | 375 | Meth 95 |

Method 114
5-N-t-Butylcarbamoyl-2-chloro-4-(4-chlorophenoxy)pyrimidine

Sodium hydride (105 mg, 2.63 mmol) was added to a solution of 4-chlorophenol (338 mg, 2.63 mmol) in dry THF (10 ml). When effervescence had stopped, this solution was slowly added to a solution of 5-N-t-butylcarbamoyl-2,4-dichloropyrimidine (Method 79; 680 mg, 2.74 mmol) in dry THF (15 ml). The reaction mixture was stirred at ambient temperature for 2 hours. The solvent was removed by evaporation and the resulting solid was suspended in diethyl ether. The insolubles were removed by filtration and the filtrate was washed with 2M sodium hydroxide solution, citric acid solution, water and brine and then dried. The volatiles were removed by evaporation to give the title compound (880 mg, 99%). M/z: 339.

Method 115
2-Chloro-4-(4-chlorophenoxy)-5-cyanopyrimidine

A solution of 5-N-t-butylcarbamoyl-2-chloro-4-(4-chlorophenoxy)pyrimidine (Method 114; 200 mg, 0.59 mmol) in thionyl chloride (5 ml, 69 mmol) was heated at reflux (95° C.) for 18 hours. The thionyl chloride was removed by evaporation to give the title compound (210 mg). NMR: 7.35 (d, 2H), 7.55 (d, 2H), 9.20 (s, 1H).

Method 116
4-[N-(2,3-Epoxypropyl)sulphamoyl]nitrobenzene p-Nitrobenzene sulphonamide (6.06 g, 30 mmol) was added portionwise to a solution of sodium hydroxide (1.32 g, 33 mmol) in water (60 ml) at room temperature. Epibromohydrin (4.5 g, 33 mmol) was added quickly dropwise and the solution stirred at room temperature for 24 hours. The mixture was acidified to pH 1 with 2M hydrochloric acid and extracted with DCM (2×30 ml). The combined organic extracts were dried with sodium sulphate, filtered and the volatiles removed by evaporation. The resulting yellow oil was purified by chromatography on silica eluting with DCM/methanol (100:0) increasing in polarity to (99:1) to give the title compound as a pale yellow solid (2.5 g, 32%); NMR (CDCl3) 2.65 (m, 1H), 2.80 (t, 1H), 3.10 (m, 2H), 3.50 (m, 1H), 5.08 (brs, 1H), 8.08 (d, 2H), 8.38 (d, 2H); m/z: 257.

Method 117
4-[N-(2-Hydroxy-3-piperidinopropyl)sulphamoyl]nitrobenzene

4-[N-(2,3-Epoxypropyl)sulphamoyl]nitrobenzene (Method 116, 1 g, 3.88 mmol) and piperidine (0.34 g, 4 mmol) in 1-propanol (75 ml) were heated at reflux for 20 hours. The mixture was cooled and the solvent evaporated. The resulting yellow oil was triturated with diethyl ether collected by filtration and dried under vacuum to give the title compound 1.2 g (90%). NMR: 1.26–1.50 (m, 6H), 2.10–2.28 (m, 6H), 2.70 (dd, 1H), 2.90 (dd, 1H), 3.55 (m, 1H), 8.04 (d, 2H), 8.40 (d, 2H); m/z: 344.

Method 118
4-[N-(2-Hydroxy-3-piperidinopropyl)sulphamoyl]aniline

Ammonium formate (1.1 g, 17.46 mmol) followed by a slurry of 10% palladium on carbon catalyst (0.7 g) in ethanol was added in portions to a suspension of 4-[N-(2-Hydroxy-3-piperidinopropyl)sulphamoyl]nitrobenzene (Method 117; 1.2 g, 3.5 mmol) in ethanol (100 ml). The mixture was heated at reflux under nitrogen for 2 hours. The mixture was cooled and the catalyst was removed by filtration through diatomaceous earth. The filter pad was washed with ethanol and the combined filtrates were evaporated. The residue was triturated with diethyl ether, collected by filtration and dried, to give the title compound (0.93 g, 85%) as a pale green solid. NMR: 1.3–1.5 (m, 6H), 2.10–2.32 (m, 6H), 2.60 (m, 1H), 2.75 (m, 1H), 3.52 (m, 1H), 4.50 (brs, 1H), 5.85 (s, 2H), 6.59 (d, 2H), 6.98 (brs, 1H), 7.39 (d, 2H); m/z: 314.

Method 119
4-[4-(2-Acetoxyethylpiperazin-1-yl)]-5-cyano-2-{4-[N-(3-methoxypropyl)sulphamoyl]anilino}pyrimidine Thionyl chloride (1.5 ml) was added to 4-[4-(2-acetoxyethylpiperazin-1-yl)]-5-N-t-butylcarbamoyl-2-{4-[N-(3-methoxypropyl)sulphamoyl]anilino}pyrimidine (Method 120; 570 mg), and the reaction was heated at 80° C. for 3 hours. The mixture was cooled, the volatiles evaporated, the residue triturated with ethyl acetate and collected by filtration to give the title compound (290 mg). M/z 518.

Method 120
4-[4-(2-Acetoxyethylpiperazin-1-yl)]-5-N-t-butylcarbamoyl-2-{4-[N-(3-methoxypropyl)sulphamoyl]anilino}pyrimidine 5-N-t-Butylcarbamoyl-4-[4-(2-hydroxyethylpiperazin-1-yl)]-2-{4-[N-(3-methoxypropyl)sulphamoyl]anilino}pyrimidine (Method 121; 1 g) was dissolved in pyridine (5 ml) at room temperature, 4-dimethylaminopyridine (~5 mg) was added, followed by dropwise addition of acetic anhydride (0.29 ml, 3 mmol). The reaction mixture was stirred for 18 hours. The volatiles were evaporated, water added and the reaction extracted with EtOAc (2×20 ml), washed with brine, dried and evaporated to give a gum (400 mg). The residue was dissolved in DCM (10 ml), triethylamine was added (300 μl, 4.1 mmol) followed by dropwise addition of acetyl chloride (100 μl, 1.15 mmol). The reaction was stirred at room temperature for 4 hours, then the volatiles were evaporated. The residue was suspended in ethyl acetate, the insolubles were removed by filtration and the filtrate evaporated to give the title compound as an oil (570 mg) which was used without further purification.

Method 121
5-N-t-Butylcarbamoyl-4-[4-(2-hydroxyethylpiperazin-1-yl)]-2-{4-[N-(3-methoxypropyl)sulphamoyl]anilino}pyrimidine 5-N-t-Butylcarbamoyl-2-chloro-4-[4-(2-hydroxyethyl) piperazin-1-yl]pyrimidine (Method 80, 1.5 mmol) and 4-[N-(3-methoxypropyl)sulphamoyl]aniline (Method 4; 330 mg, 1.35 mmol) in 2-butanol (5 ml) were heated at 95° C. for 5 minutes. 1M Ethereal hydrogen chloride (1.5 ml, 1.5 mmol) was added and heating continued at 95° C. for 2 hours. The volatiles were evaporated, the residue triturated with ethyl acetate and collected by filtration to give the title compound (1 g). M/z 550.

Example 133

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I):

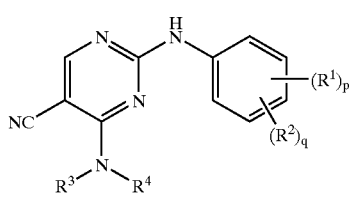

(I)

wherein:
R¹ is halo, nitro, cyano, hydroxy, amino, carboxy, carbamoyl, mercapto, $C_{1-6}$alkyl, $C_{2-6}$alkenyl or $C_{2-6}$alkynyl;

p is 0–4; wherein the values of R¹ may be the same or different;

R² is sulphamoyl or a group B-E-;

q is 0–2; wherein the values of R² maybe the same or different; and wherein p+q=1–5;

R³ is hydrogen, $C_{1-6}$alkyl, $C_{2-6}$alkenyl, $C_{2-6}$alkynyl or $C_{3-8}$cycloalkyl; wherein R³ may be optionally substituted on carbon by one or more M;

R⁴ is $C_{1-6}$alkyl, $C_{2-6}$alkenyl, $C_{2-6}$alkynyl, $C_{3-8}$cycloalkyl or heterocyclyl; wherein R⁴ may be optionally substituted by one or more M; wherein if said heterocyclyl contains an —NH— moiety that nitrogen may be optionally substituted by a group selected from Z;

or R³ and R⁴ together with the nitrogen to which they are attached form a heterocyclic ring optionally substituted on carbon by one or more M; wherein if said heterocyclic ring contains an —NH— moiety that nitrogen may be optionally substituted by a group selected from Q;

B is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, a heterocyclic group, phenyl$C_{1-6}$alkyl or (heterocyclic group)$C_{1-6}$alkyl; wherein B may be optionally substituted on carbon by one or more D; and wherein if said heterocyclic group contains an —NH— moiety that nitrogen may be optionally substituted by a group selected from G;

E is —C(O)—, —N(Rᵃ)C(O)—, —C(O)N(Rᵃ)—, —S(O)ᵣ—, —SO₂N(Rᵃ)— or —N(Rᵃ)SO₂—; wherein Rᵃ is hydrogen or $C_{1-6}$alkyl optionally substituted by one or more D and r is 1–2;

D is independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)₂ amino, $C_{1-6}$alkanoylamino, N-($C_{1-6}$alkyl)carbamoyl, N,N-($C_{1-6}$alkyl)₂carbamoyl, $C_{1-6}$alkylS(O)ₐ wherein a is 0 to 2, $C_{1-6}$alkoxycarbonyl, N-($C_{1-6}$alkyl)sulphamoyl and N,N-($C_{1-6}$alkyl)₂sulphamoyl; wherein D may be optionally substituted on carbon by one or more V;

M is independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)₂ amino, $C_{1-6}$alkanoylamino, N-($C_{1-6}$alkyl)carbamoyl, N,N-($C_{1-6}$alkyl)₂carbamoyl, $C_{1-6}$alkylS(O)ₐ wherein a is 0 to 2, $C_{1-6}$alkoxycarbonyl, N-($C_{1-6}$alkyl) sulphamoyl, N,N-($C_{1-6}$alkyl)₂sulphamoyl, $C_{3-8}$cycloalkyl, phenyl or a heterocyclic group; wherein M may be optionally substituted on carbon by one or more P; and wherein if said heterocyclic group contains an —NH— moiety that nitrogen may be optionally substituted by a group selected from T;

P, X and V are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and G, Q, T and Z are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl) carbamoyl, benzyl, benzyloxycarbonyl, benzoyl and phenylsulphonyl wherein G, Q and T may be independently optionally substituted on carbon by one or more X;

or a pharmaceutically acceptable salt thereof.

2. A compound of formula (I) as claimed in claim 1 wherein p is 0; or a pharmaceutically acceptable salt thereof.

3. A compound of formula (I) as claimed in claim 1 wherein R² is sulphamoyl or a group B-E-; wherein B is selected from $C_{1-6}$alkyl, $C_{2-6}$alkenyl, $C_{2-6}$alkynyl or (heterocyclic group)$C_{1-6}$alkyl; wherein B may be optionally substituted on carbon by one or more D; and wherein if said heterocyclic group contains an —NH— moiety that nitrogen may be optionally substituted by a group selected from G;

E is —S(O)ᵣ— or —N(Rᵃ)SO₂—; wherein Rᵃ is hydrogen or $C_{1-6}$alkyl and r is 2;

D is independently selected from halo, cyano, hydroxy, amino, $C_{1-6}$alkyl, $C_{1-6}$alkoxy, N-($C_{1-6}$alkyl)amino, N,N-($C_{1-6}$alkyl)₂amino, $C_{1-6}$alkanoylamino and $C_{1-6}$alkylS(O)ₐ wherein a is 0 to 2; wherein D may be optionally substituted on carbon by a group selected from V;

V is selected from hydroxy and dimethylamino; and

G is selected from $C_{1-4}$alkyl;

or a pharmaceutically acceptable salt thereof.

4. A compound of formula (I) as claimed in claim 1 wherein q is 1; or a pharmaceutically acceptable salt thereof.

5. A compound of formula (I) as claimed in claim 1 wherein R³ is hydrogen or $C_{1-6}$alkyl; wherein R³ may be optionally substituted by one or more M; and R⁴ is $C_{1-6}$alkyl, $C_{2-6}$alkenyl, $C_{2-6}$alkynyl or $C_{3-8}$cycloalkyl; wherein R⁴ may be optionally substituted by one or more M;

or R³ and R⁴ together with the nitrogen to which they are attached form a heterocyclic ring optionally substituted on carbon by one or more M; wherein if said heterocyclic ring contains an —NH— moiety that nitrogen may be optionally substituted by a group selected from Q;

M is independently selected from halo, cyano, hydroxy, $C_{1-6}$alkyl, $C_{1-6}$alkoxy, N,N-($C_{1-6}$alkyl)₂amino, $C_{1-6}$alkoxycarbonyl, $C_{3-8}$cycloalkyl or a heterocyclic group; wherein M may be optionally substituted on carbon by a group selected from P;

P and X are independently selected from hydroxy and methoxy; and

Q is selected from $C_{1-4}$alkyl, $C_{1-4}$alkylsulphonyl or $C_{1-4}$alkoxycarbonyl; wherein Q may be optionally substituted on carbon by one or more X;

or a pharmaceutically acceptable salt thereof.

6. A compound of formula (I) as depicted in claim 1 wherein:

p is 0;

$R^2$ is sulphamoyl, mesyl, ethylsulphonyl, 2-ethoxyethylsulphonyl, propylsulphonyl, 3-isopropylaminopropylsulphonyl, 4-isopropylaminobutylsulphonyl, N-(tetrahydrofur-2-ylmethyl)sulphamoyl, N-(pyrid-3-ylmethyl) sulphamoyl, N-(pyrid-2-ylmethyl)sulphamoyl, N-(1,4-dioxan-2-ylmethyl)sulphamoyl, N-(methyl) sulphamoyl, N-(2-methoxyethyl)sulphamoyl, N-(2-ethylthioethyl)sulphamoyl, N-(2-morpholinoethyl) sulphamoyl, N-(2-piperidinoethyl)sulphamoyl, N-(2-pyrid-2-ylethyl)sulphamoyl, N-(2-pyrrolidin-1-ylethyl) sulphamoyl, N-(2-imidazol-4-ylethyl)sulphamoyl, N-(2-isopropylaminoethyl)sulphamoyl, N-(2-mesylethyl)sulphamoyl, N-[2-(2-hydroxyethoxy)ethyl] sulphamoyl, N-[2-(1-ethylpyrrolidin-2-yl)ethyl] sulphamoyl, N-(2-pyrid-2-ylethyl)sulphamoyl, N-(2-diethylaminoethyl)sulphamoyl, N-(2-pyrid-4-ylethyl) sulphamoyl, N-(2-acetamidoethyl)sulphamoyl, N-(2-dimethylaminoethyl)sulphamoyl, N-[2-(5-methyl-1,3,4-triazol-2-yl)ethyl]sulphamoyl, N-(2-hydroxyethyl) sulphamoyl, N-(2-cyanoethyl)sulphamoyl, N-(2-diethylaminoethyl)-N-(methyl)sulphamoyl, N-(2-methoxyethyl)-N-(methyl)sulphamoyl, N-(2,2,2-trifluoroethyl)sulphamoyl, N-(3-hydroxy-2,2-dimethylpropyl)sulphamoyl, N-(3-isopropylaminopropyl)sulphamoyl, N-(3-methoxypropyl)sulphamoyl, N-(3-imidazol-1-ylpropyl)sulphamoyl, N-(2-hydroxy-3-aminopropyl) sulphamoyl, N-(3-hydroxypropyl)sulphamoyl, N-(3-ethoxypropyl)sulphamoyl, N-[3-(2-dimethylaminoethyl)propyl]sulphamoyl, N-(3-morpholinopropyl)sulphamoyl, N-(2-hydroxypropyl) sulphamoyl, N-(2-hydroxy-3-piperidinopropyl) sulphamoyl, N-(3-piperidinopropyl)-N-(methyl) sulphamoyl, N-(2-hydroxybutyl)sulphamoyl, N-(pentyl)sulphamoyl, N-(5-hydroxypentyl) sulphamoyl, N-(allyl)sulphamoyl or N-(2-propynyl) sulphamoyl;

q is 1 and $R^2$ is para to the amino group in the aniline of formula (I); and $R^3$ and $R^4$ together with the nitrogen to which they are attached form isobutylamino, ethylamino, 2-fluoroethylamino, 3-ethoxypropylamino, butylamino, 2,2,2-trifluoroethylamino, 3-morpholinopropylamino, cyclopropylamino, cyclopropylmethylamino, cyclohexylamino, tetrahydrofur-2-ylmethylamino, 2-dimethylaminoethylamino, cyanomethylamino, pyrid-3-ylmethylamino, butoxycarbonylmethylamino, 2-(methoxycarbonyl)ethylamino, 2-hydroxyethylamino, methylamino, 2-propynylamino, 2-methoxyethylamino, 2-imidazol-4-ylethylamino, 2-(2-hydroxyethoxy)ethylamino, 2,3-dihydroxypropylamino, 2,2-dimethyldioxolan-4ylmethylamino, propylamino, N-methyl-N-allylamino, N-methyl-N-ethoxycarbonylmethylamino, N-methyl-N-(2-cyanoethyl)amino, diethylamino, N-methyl-N-(2-methoxyethyl)amino, bis-(2-cyanoethyl)amino, N-ethyl-N-cyclohexylamino, N-methyl-N-(2,2,2-trifluoroethyl)amino, N-methyl-N-(2-propynyl)amino, morpholino, 2,6-dimethylmorpholino, 3,5-dimethylpiperidino, piperidino, 4-(2-methoxyethyl)piperazin-1-yl, 4-methylpiperazin-1-yl, 4-isopropylpiperazin-1-yl, 4-ethylsulphonylpiperazin-1-yl, 4-ethoxycarbonylpiperazin-1-yl, 4-(2-hydroxyethyl) piperazin-1-yl, and 3-hydroxypyrrolidin-1-yl;

or a pharmaceutically acceptable salt thereof.

7. A compound of formula (I) selected from:

5-Cyano-4-n-butylamino-2-(4-mesylanilino)pyrimidine;

5-Cyano-4-ethylamino-2-{4-[N-(2-methoxyethyl) sulphamoyl]anilino}pyrimidine;

5-Cyano-4-ethylamino-2-{4-[N-(3-methoxypropyl) sulphamoyl]anilino}pyrimidine;

5-Cyano-4-cyclopropylamino-2-{4-[N-(2-methoxyethyl) sulphamoyl]anilino}pyrimidine;

5-Cyano-4-cyclopropylamino-2-{4-[N-(3-methoxypropyl)sulphamoyl]anilino}pyrimidine;

5-Cyano-4-cyclopropylamino-2-[4-(ethylsulphonyl) anilino]pyrimidine;

5-Cyano-4-cyclopropylamino-2-(4-mesylanilino) pyrimidine;

5-Cyano-4-ethylamino-2-[4-(N-methylsulphamoyl) anilino]pyrimidine;

5-Cyano-4-cyclopropylamino-2-{4-[N-(2-methoxyethyl)-N-(methyl)sulphamoyl] anilino}pyrimidine; and 5-Cyano-4-(ethylamino)-2-(4-ethylsulphonylanilino) pyrimidine;

or a pharmaceutically acceptable salt thereof.

8. A pharmaceutical composition which comprises a compound of the formula (I), or a pharmaceutically acceptable salt thereof, as claimed in any one of claims 1–7 in association with a pharmaceutically-acceptable diluent or carrier.

9. A method for inhibiting cyclin-dependent kinase CDK2, CDK4 or CDK6 in a warm-blooded animal, which comprises administering to said animal an inhibitory amount of a compound of formula (I) or a pharmaceutically acceptable salt thereof as claimed in any one of claims 1–7.

10. A process for preparing a compound of formula (I) or or a pharmaceutically acceptable salt thereof which process (wherein $R^1$, $R^2$, $R^3$, $R^4$, p and q are, unless otherwise specified, as defined in claim 1) comprises of:

a) reaction of a pyrimidine of formula (II):

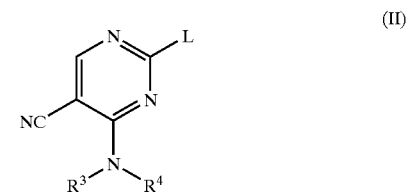

(II)

wherein L is a displaceable group; with an aniline of formula (III):

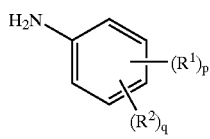

(b) reacting a pyrimidine of formula (IV):

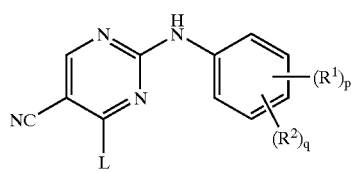
(IV)

wherein L is a displaceable group; with an amine of formula (V):

R³R⁴NH  (V)

c) reacting a compound of formula (VI):

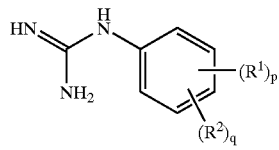
(VI)

with a compound of formula (VII):

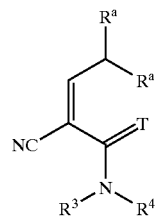
(VII)

wherein T is O or S; $R^a$ may be the same or different and is selected from $C_{1-6}$alkyl;

d) for compounds of formula (I) where $R^2$ is sulphamoyl or a group B-E- and E is —NHSO₂—; reacting a pyrimidine of formula (VIII):

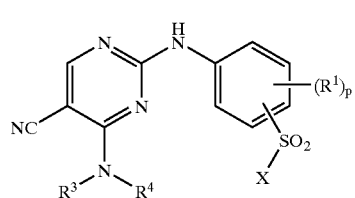
(VIII)

wherein X is a displaceable group; with an amine of formula (IX):

B—NH₂  (IX)

or e) by converting a compound of formula (X):

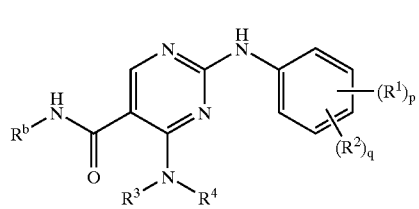
(X)

wherein $R^b$ is hydrogen or t-butyl; into a compound of formula (I); and thereafter optionally:

i) converting a compound of the formula (I) into another compound of the formula (I);
ii) removing any protecting groups;
iii) forming a pharmaceutically acceptable salt.

* * * * *